US010858326B2

(12) United States Patent
Blake et al.

(10) Patent No.: US 10,858,326 B2
(45) Date of Patent: Dec. 8, 2020

(54) OXAZOLINE PSEUDODIMERS, PHARMACEUTICAL COMPOSITIONS AND THE USE THEREOF

(71) Applicant: PURDUE PHARMA L.P., Stamford, CT (US)

(72) Inventors: Paul Blake, Newtown, PA (US); Laykea Tafesse, Robbinsville, NJ (US)

(73) Assignee: PURDUE PHARMA L.P., Stamford, CT (US)

( * ) Notice: Subject to any disclaimer, the term of this patent is extended or adjusted under 35 U.S.C. 154(b) by 0 days.

(21) Appl. No.: 16/098,494

(22) PCT Filed: May 4, 2017

(86) PCT No.: PCT/US2017/031071

§ 371 (c)(1),
(2) Date: Nov. 2, 2018

(87) PCT Pub. No.: WO2017/192858

PCT Pub. Date: Nov. 9, 2017

(65) Prior Publication Data

US 2019/0144400 A1 May 16, 2019

Related U.S. Application Data

(60) Provisional application No. 62/331,710, filed on May 4, 2016.

(51) Int. Cl.

| | |
|---|---|
| ***C07D 263/28*** | (2006.01) |
| ***C07D 413/06*** | (2006.01) |
| ***A61P 25/04*** | (2006.01) |

(52) U.S. Cl.
CPC ............ *C07D 263/28* (2013.01); *A61P 25/04* (2018.01); *C07D 413/06* (2013.01)

(58) Field of Classification Search
CPC .............................. A61P 25/04; C07D 263/28
See application file for complete search history.

(56) References Cited

U.S. PATENT DOCUMENTS

| | | | |
|---|---|---|---|
| 3,536,809 | A | 10/1970 | Norman |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall, I et al. |
| 5,120,548 | A | 6/1992 | McClelland et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,698,155 | A | 12/1997 | Grosswald et al. |
| 5,733,566 | A | 3/1998 | Lewis |
| 7,902,238 | B2 | 3/2011 | Galley et al. |
| 2009/0105307 | A1 | 4/2009 | Galley et al. |
| 2010/0120864 | A1 | 5/2010 | Galley et al. |
| 2010/0311798 | A1 | 12/2010 | Decoret et al. |
| 2012/0165294 | A1 | 6/2012 | Galley et al. |

FOREIGN PATENT DOCUMENTS

WO WO-2017192858 A1 11/2017

OTHER PUBLICATIONS

Zocher et al (2007), STN International (Columbus, Ohio) HCAPLUS database, Accession No. 2007: 155050.*
Werner et al (2003), STN International (Columbus, Ohio), HCAPLUS database, Accession No. 2003: 922779.*
Bartho, L., et al., "Involvement of Capsaicin-sensitive Neurones in Hyperalgesia and Enhanced Opioid Antinociception in Inflammation," Naunyn-Schmiedeberg's Archives of Pharmacology 342(6):666-670, Springer Verlag, Germany (Dec. 1990).
Borowsky, B., et al., "Trace Amines: Identification of a Family of Mammalian G Protein-coupled Receptors," Proceedings of the National Academy of Sciences of the United States of America, 98(16):8966-8971, National Academy of Sciences, United States (Jul. 2001).
Buchwald, H., et al., "Long-term, Continuous Intravenous Heparin Administration by an Implantable Infusion Pump in Ambulatory Patients with Recurrent Venous Thrombosis," Surgery 88(4):507-516, Mosby, United States (Oct. 1980).
D'Amour, F.E. and Smith, D.L., "A Method for Determining Loss of Pain Sensation," Journal of Pharmacology and Experimental Therapeutics 72(1):74-79, the British Pharmaceutical Society, England (May 1941).
During, M.J., et al., "Controlled Release of Dopamine From a Polymeric Brain Implant: in Vivo Characterization," Annals of Neurology 25(4):351-356, Wiley-Liss, United States (Apr. 1989).
Foley, K.M., "Pain, Problems of Overarching Importance Which Transcend Organ Systems," in Cecil Textbook of Medicine, 20th Edition, Bennett, J.C. and Plum, F., eds., pp. 100-107, WB Saunders Company,United States (1996).

(Continued)

*Primary Examiner* — Golam M Shameem
(74) *Attorney, Agent, or Firm* — Sterne, Kessler, Goldstein & Fox, P.L.L.C.

(57) ABSTRACT

The present disclosure is directed to oxazoline mono- and hetero-pseudodimer compounds, such as compounds of Formula (I) or pharmaceutically acceptable salts or solvates thereof:

I

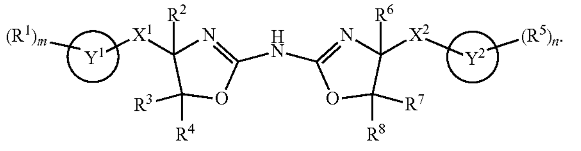

These compounds are useful for treating pain. The present disclosure also relates to pharmaceutical compositions comprising a pharmaceutically acceptable carrier and a therapeutically effective amount of a compound of Formula (I) or (II) or a pharmaceutically acceptable salt or solvate thereof.

19 Claims, 1 Drawing Sheet

(56) References Cited

OTHER PUBLICATIONS

Galley, G., et al., "Discovery and Characterization of 2-Aminooxazolines as Highly Potent, Selective, and Orally Active TAAR1 Agonists," ACS Medicinal Chemistry Letters, 7(2):192-197, American Chemical Society, United States (Dec. 2015).
Goodson, J.M., "Dental Applications," in Medical Applications of Controlled Release, vol. 2, Langer, R.S. and Wise, D.L., eds., pp. 115-138, CRC Press, Inc., United States (1984).
Grupp, I.L., et al., "Protection Against Hypoxia-reoxygenation in the Absence of Poly (ADP-ribose) Synthetase in Isolated Working Hearts," Journal of Molecular and Cellular Cardiology 31(1):297-303, Academic Press, England (Jan. 1999).
Hargreaves, K., et al., "A New and Sensitive Method for Measuring Thermal Nociception in Cutaneous Hyperalgesia," Pain 32(1):77-88, Lippincott Williams & Wilkins, United States (January1988).
Howard, M.A. 3rd., "Intracerebral Drug Delivery in Rats With Lesion-induced Memory Deficits," Journal of Neurosurgery 71(1):105-112, American Association of Neurological Surgeons, United States (Jul. 1989).
Kim, S.H., et al., "An Experimental Model for Peripheral Neuropathy Produced by Segmental Spinal Nerve Ligation in the Rat," Pain 50(3):355-363, Lippincott Williams & Wilkins, United States (Sep. 1992).
Langer, R., "New Methods of Drug Delivery," Science 249(4976):1527-1533, American Association for the Advancement of Science, United States (Sep. 1990).
Levy, R.J., et al., "Inhibition of Calcification of Bioprosthetic Heart Valves by Local Controlled-release Diphosphonate," Science 228(4696):190-192, American Association for the Advancement of Science, United States (Apr. 1985).
Lindemann, L., et al., "Trace Amine-associated Receptors Form Structurally and Functionally Distinct Subfamilies of Novel G Protein-coupled Receptors," Genomics, 85(3):372-385, Academic Press, United States (Mar. 2005).
Langer, R and Peppas, N., "Chemical and Physical Structure of Polymers as Carriers for Controlled Release of Bioactive Agents: A Review," Journal of Macromolecular Science, Part C Polymer Reviews, 23(1): 61-126 (1983).
Revel, F.G., et al., "TAAR1 Activation Modulates Monoaminergic Neurotransmission, Preventing Hyperdopaminergic and Hypoglutamatergic Activity," Proceedings of the National Academy of Sciences of the United States of America, 108(20):8485-8490, National Academy of Sciences, United States (May 2011).
Saudek, C.D., et al., "A Preliminary Trial of the Programmable Implantable Medication System for Insulin Delivery," the New England Journal of Medicine 321(9):574-579, Massachusetts Medical Society, United States (Aug. 1989).
Sefton, M.V., "Implantable Pumps," Critical Reviews in Biomedical Engineering 14(3):201-240, Begell House, United States (1987).
Seltzer, Z., et al., "A Novel Behavioral Model of Neuropathic Pain Disorders Produced in Rats by Partial Sciatic Nerve Injury," Pain 43(2):205-218, Lippincott Williams & Wilkins, United States (Nov. 1990).
Stein, C., et al., "Unilateral Inflammation of the Hindpaw in Rats as a Model of Prolonged Noxious Stimulation: Alterations in Behavior and Nociceptive Thresholds," Pharmacology, Biochemistry, and Behavior 31(2):451-455, Elsevier, United States (Oct. 1988).
Torbati, D., et al., "Effect of Hypothermia on Ventilation in Anesthetized, Spontaneously Breathing Rats: Theoretical Implications for Mechanical Ventilation," Intensive Care Medicine 26(5):585-591, Springer-Verlag GmbH & Co., Germany (May 2000).
Treat, J., et al., "Liposome Encapsulated Doxorubicin Preliminary Results of Phase I and Phase II Trials," in Liposomes in the Therapy of Infectious Diseases and Cancer, Lopez-Berestein, G.and Fidler, I.J., eds., pp. 353-365, Alan R. Liss, Inc.,United States(1989).
Woolfe, G. and MacDonald, A.D., "The Evaluation of the Analgesic Action of Pethidine Hydrochloride (Demerol)," Journal of Pharmacology and Experimental Therapeutics 80(3):300-307, the British Pharmacological Society, England (Mar. 1944).
Xie, Z and Miller, G.M., "Trace Amine-associated Receptor 1 as a Monoaminergic Modulator in Brain," Biochemical Pharmacology, 78(9):1095-1104, Elsevier Science, England (Nov. 2009).
International Search Report and Written Opinion for International Application No. PCT/US2017/031071, European Patent Office, Germany, dated Jul. 12, 2017, 11 pages.
International Preliminary Report on Patentability for International Application No. PCT/US2017031071, International Bureau of WIPO, dated Nov. 6, 2018, 8 pages.
Gissibl, A., et al., "Cu(II)-Aza(bisoxazoline)-Catalyzed Asymmetric Benzoylations," Organic Letters 7(12):2325-2328, American Chemistry Society, United States (2005).
Hager, M., et al., "The importance of 1:1 and 1:2 metal-ligand species in Chiral copper(II)-bis(oxazoline) complexes for catalytic activity," Tetrahedron Asymmetry 21(9-10):1194-1198, Pergamon Press Ltd., United States (2010).
Zocher, E., et al., "Threshold CID Investigation of Isomeric Cu(I) Azabox Complexes," Inorganic Chemistry 46(26):11366-11370, American Chemistry Society, United States (2007).

* cited by examiner

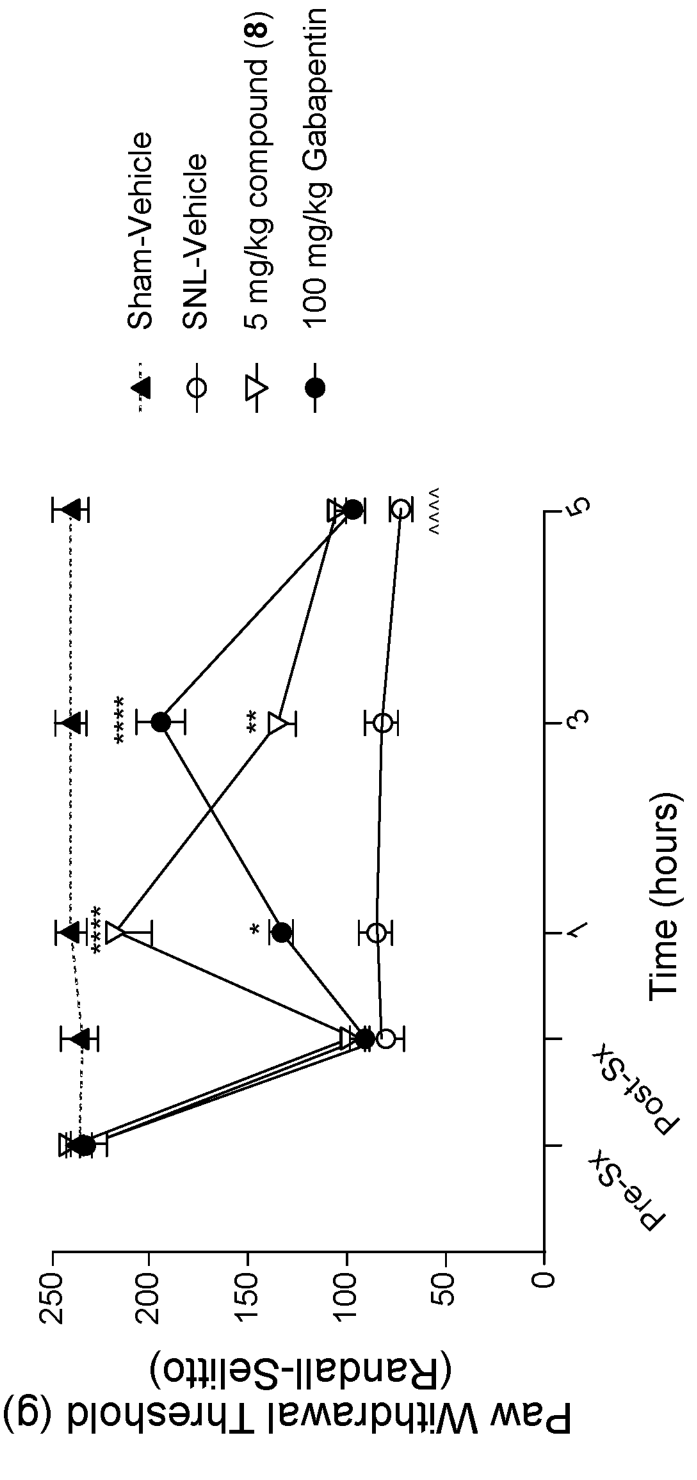
^^^^P< 0.0001 (SNL-Vehicle vs Sham-Vehicle; model development);
**P< 0.0001, P< 0.01, and *P<0.05 compared to SNL-Vehicle control.

OXAZOLINE PSEUDODIMERS, PHARMACEUTICAL COMPOSITIONS AND THE USE THEREOF

BACKGROUND OF THE INVENTION

This invention is in the field of medicinal chemistry. In particular, novel oxazoline mono- and hetero-pseudodimer compounds are disclosed. These compounds have pharmaceutical activity, and are useful for treating conditions, such as, pain.

Pain is the most common symptom for which patients seek medical advice and treatment. While acute pain is usually self-limited, chronic pain can persist for 3 months or longer and lead to significant changes in a patient's personality, lifestyle, functional ability and overall quality of life (K. M. Foley, Pain, in *Cecil Textbook of Medicine* 100-107, J. C. Bennett and F. Plum eds., 20th ed. 1996). Chronic pain can occur after a known injury or disease, or it can occur without any known physical cause. Moreover, it can be accompanied by known tissue pathology, such as chronic inflammation that occurs in some types of arthritis, or it can occur long after the healing of the injured tissue which is suspected or known to be the cause of the chronic pain. Chronic pain is a very general concept and there are several varieties of chronic pain related to the musculoskeletal system, visceral organs, skin, and nervous system.

Chronic pain can be classified as either nociceptive or neuropathic. Nociceptive pain includes tissue injury-induced pain and inflammatory pain, such as, that associated with arthritis. Neuropathic pain is caused by damage to the peripheral or central nervous system and is maintained by aberrant somatosensory processing.

Chronic pain includes, for example, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic pain, and idiopathic pain syndromes.

Neuropathic pain is a common variety of chronic pain. It can be defined as pain that results from an abnormal functioning of the peripheral and/or central nervous system. A critical component of this abnormal functioning is an exaggerated response of pain-related nerve cells either in the periphery or in the central nervous system. An example is pain from causalgia wherein even a light touch to the skin is felt as an excruciating burning pain.

Nociceptive pain has been traditionally managed by administering non-opioid analgesics, such as acetylsalicylic acid, choline magnesium trisalicylate, acetaminophen, ibuprofen, fenoprofen, diflusinal, and naproxen; or opioid analgesics, including morphine, hydromorphone, methadone, levorphanol, fentanyl, oxycodone, and oxymorphone. In addition to the above-listed treatments, neuropathic pain, which can be difficult to treat, has also been treated with anti-epileptics (e.g. gabapentin, carbamazepine, valproic acid, topiramate, phenyloin), NMDA antagonists (e.g. ketamine, dextromethorphan), topical lidocaine (for post-herpetic neuralgia), and tricyclic antidepressants (e.g. fluoxetine, sertraline and amitriptyline).

Many chronic pain patients respond poorly to current pain therapies, and the development of resistance or insensitivity to the analgesics is common. In addition, many of the currently available treatments have undesirable side effects.

There is still a need to develop novel therapies for treating pain, especially chronic pain (e.g., neuropathic pain).

BRIEF SUMMARY OF THE INVENTION

The present inventors have discovered that novel oxazoline mono- and hetero-pseudodimer compounds are useful in the treatment of pain, especially neuropathic pain. In certain embodiments, the oxazoline mono- or hetero-pseudodimer compound of the present disclosure acts as a TAAR1 agonist or partial agonist.

In one aspect, the present disclosure provides the compounds of Formula (I):

I

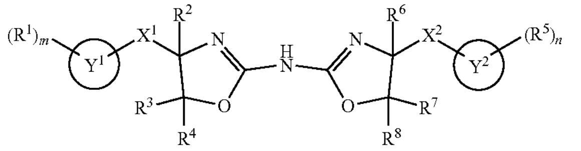

or a pharmaceutically acceptable salt or solvate thereof, wherein each $R^1$ and each $R^5$ are independently:
- deuterium,
- tritium,
- lower alkyl,
- lower alkoxy,
- lower alkyl substituted by one or more same or different halogens,
- lower alkoxy substituted by one or more same or different halogens,
- halogen,
- phenyl unsubstituted or substituted by one or more same or different halogens,
- phenyloxy,
- benzyl,
- benzyloxy,
- COO-lower alkyl,
- $—O—(CH_2)_o—$O-lower alkyl,
- —NH-cycloalkyl,
- cycloalkyl,
- piperidin-1-yl, or
- tetrahydropyran-4-yloxy;

$X^1$ and $X^2$ are each independently a bond, $—CH(R^{20})—$, $—CH(R^{20})CH(R^{21})—$, $—OCH(R^{20})—$, $—N(R^{20})CH(R^{21})—$, $—CH_2OCH(R^{20})—$, $—CH_2CH_2CH_2—$, $—SCH(R^{20})—$, $—S(O)_2CH(R^{20})—$, $—CH_2SCH_2—$, $—CH_2N(R^{20})CH_2—$, -cycloalkyl-$CH_2$— or $—Si(R^{20})(R^{21})CH_2—$, wherein $R^{20}$ and $R^{21}$ are each independently hydrogen, lower alkyl, lower alkyl substituted by one or more same or different halogens, or benzyl unsubstituted or substituted by one or more same or different substituents selected from the group consisting of alkoxy and halogen;

$R^2$ and $R^6$ are each independently hydrogen, phenyl or lower alkyl;

$R^3$, $R^4$, $R^7$, and $R^8$ are each independently hydrogen, lower alkyl, lower alkoxy, lower alkyl substituted by one or more same or different halogens, or lower alkoxy substituted by one or more same or different halogens;

$Y^1$ and $Y^2$ are each independently phenyl, naphthyl, thiophenyl, pyridinyl, cycloalkyl, 1,2,3,4-tetrahydro-naphthalen-2-yl, 2,3-dihydrobenzo[1,4]dioxin-6-yl, benzo[1,3]dioxol-5-yl, pyrimidyl, indanyl, 2,3-dihydroindol-1-yl, or 3,4-dihydro-quinolin-1-yl;

m and n are each independently 0, 1, 2 or 3; and o is 1, 2, or 3.

In one embodiment, the two oxazoline moieties, in the compounds of Formula (I) disclosed herein,

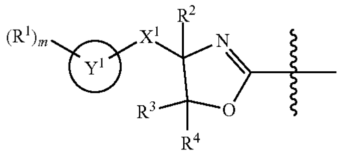

and

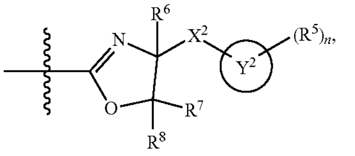

are the same. Such compounds are sometimes referred to as mono-pseudodimers in the present disclosure.

In another embodiment, the two oxazoline moieties, in the compounds of Formula (I) disclosed herein,

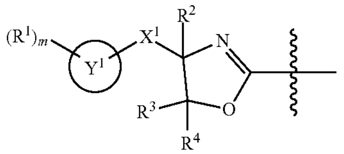

and

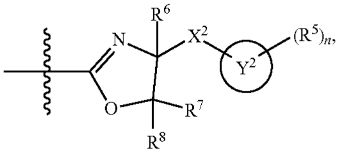

are different. Such compounds are sometimes referred to as hetero-pseudodimers in the present disclosure.

Further, the present disclosure includes all racemic mixtures, all enantiomers and/or optical isomers of the compounds disclosed herein. In addition, all tautomeric forms of the compounds described herein are also encompassed by the present disclosure. Furthermore, all polymorphic forms of the compounds described herein or pharmaceutically acceptable salts or solvates thereof are also encompassed by the present disclosure.

In another embodiment, the present disclosure relates to a compound of Formula (I-A):

I-A

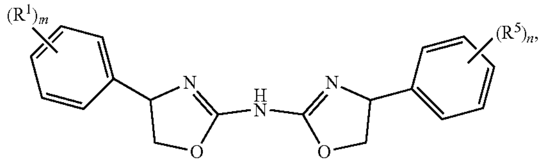

or a pharmaceutically acceptable salt or solvate thereof, wherein $R^1$, $R^5$, m, and n are as defined above for Formula (I).

In one embodiment, the present disclosure relates to a compound of Formula (I-Aa):

I-Aa

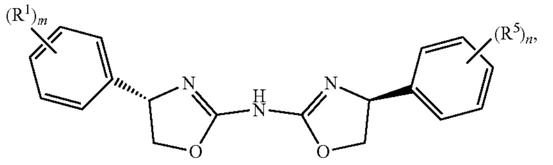

or a pharmaceutically acceptable salt or solvate thereof, wherein $R^1$, $R^5$, m, and n are as defined above for Formula (I-A).

In another embodiment, the present disclosure relates to a compound of Formula (I-Ab):

I-Ab

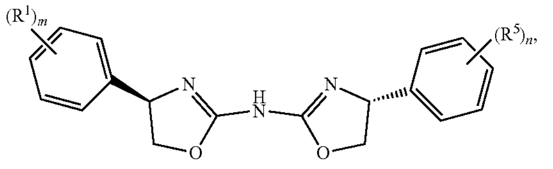

or a pharmaceutically acceptable salt or solvate thereof, wherein $R^1$, $R^5$, m, and n are as defined above for Formula (I-A).

In still another embodiment, the present disclosure relates to a compound of Formula (I-Ac):

I-Ac

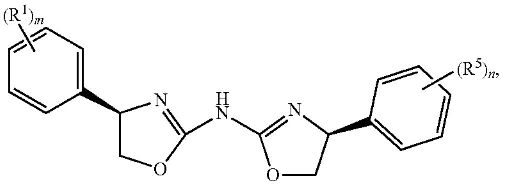

or a pharmaceutically acceptable salt or solvate thereof, wherein $R^1$, $R^5$, m, and n are as defined above for Formula (I-A).

In yet another embodiment, the present disclosure relates to a compound of Formula (I-Ad):

I-Ad

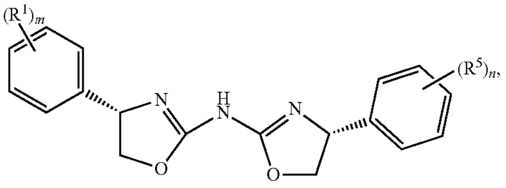

or a pharmaceutically acceptable salt or solvate thereof, wherein $R^1$, $R^5$, m, and n are as defined above for Formula (I-A).

In another embodiment, the present disclosure relates to a compound of Formula (I-B):

I-B

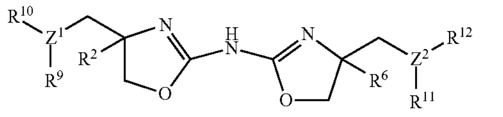

or a pharmaceutically acceptable salt or solvate thereof, wherein $Z^1$ and $Z^2$ are each independently N or CH;

$R^2$ and $R^6$ are each independently hydrogen or lower alkyl;

$R^9$ and $R^{11}$ are each independently hydrogen, lower alkyl, or benzyl unsubstituted or substituted by alkoxy or halogen; and $R^{10}$ and $R^{12}$ are each independently aryl; or $R^9$ and $R^{10}$ together with the N-atom to which they are attached form an 8- to 10-membered heterocyclic group, $R^{11}$ is each independently hydrogen, lower alkyl, or benzyl unsubstituted or substituted by alkoxy or halogen, and $R^{12}$ is aryl; or $R^{11}$ and $R^{12}$ together with the N-atom to which they are attached form an 8- to 10-membered heterocyclic group, $R^9$ is each independently hydrogen, lower alkyl, or benzyl unsubstituted or substituted by alkoxy or halogen, and $R^{10}$ is aryl;

wherein the aryl group is selected from the group consisting of phenyl, naphthyl, 1,2,3,4-tetrahydro-naphthalen-2-yl, and indanyl, and wherein the aryl group is unsubstituted or substituted by one to three substituents, independently selected from the group consisting of cycloalkyl, phenyl, phenyloxy, benzyl, benzyloxy, halogen, lower alkyl, lower alkoxy, piperidin-1-yl, lower alkyl substituted by one or more same or different halogens, and lower alkoxy substituted by one or more same or different halogens.

In another embodiment, the present disclosure relates to a compound of Formula (I-C):

I-C

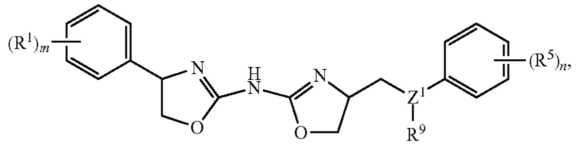

or a pharmaceutically acceptable salt or solvate thereof, wherein $Z^1$ is N or CH;

each $R^1$ and each $R^5$ are independently:

lower alkyl, lower alkoxy, lower alkyl substituted by one or more same or different halogens, lower alkoxy substituted by one or more same or different halogens, halogen, or cycloalkyl;

$R^9$ is hydrogen, lower alkyl or benzyl unsubstituted or substituted by one or more same or different substituents selected from the group consisting of alkoxy or halogen; and m and n are each independently 0, 1, 2, or 3.

In one embodiment, the present disclosure relates to a compound of Formula (I-Ca):

I-Ca

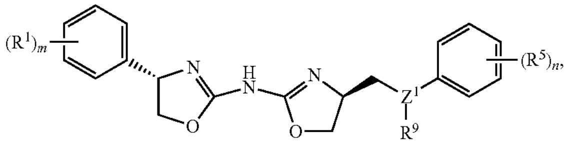

or a pharmaceutically acceptable salt or solvate thereof, wherein $R^1$, $R^5$, $R^9$, $Z^1$, m, and n are as defined above for Formula (I-C).

In another embodiment, the present disclosure relates to a compound of Formula (I-Cb):

I-Cb

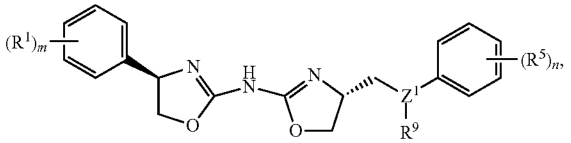

or a pharmaceutically acceptable salt or solvate thereof, wherein $R^1$, $R^5$, $R^9$, $Z^1$, m, and n are as defined above for Formula (I-C).

In yet another embodiment, the present disclosure relates to a compound of Formula (I-Cc):

I-Cc

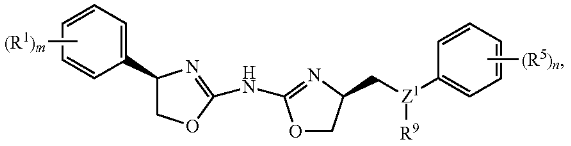

or a pharmaceutically acceptable salt or solvate thereof, wherein $R^1$, $R^5$, $R^9$, $Z^1$, m, and n are as defined above for Formula (I-C).

In still another embodiment, the present disclosure relates to a compound of Formula (I-Cd):

I-Cd

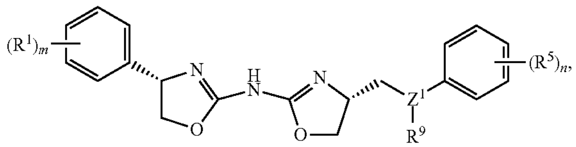

or a pharmaceutically acceptable salt or solvate thereof, wherein $R^1$, $R^5$, $R^9$, $Z^1$, m, and n are as defined above for Formula (I-C).

In one embodiment, the compounds disclosed herein are substantially pure.

The term "substantially pure" means that the compound has a purity of greater than or equal to 90%. In some embodiments, the compounds disclosed herein are substantially separated from a corresponding aminooxazoline monomer. In particular, a product containing the compounds disclosed herein comprises 20% or less of a corresponding aminooxazoline monomer. In some embodiments, the corresponding aminooxazoline monomer is present in a product containing the compounds disclosed herein in an amount of less than 15%, less than 10%, less than 5%, less than 4%, or less than 3%. In one embodiment, the present disclosure relates to the compounds described herein, or pharmaceutically acceptable salts or solvates thereof, with a purity of at least 80%, preferably at least 90%, more preferably at least 95%, most preferably at least 97%.

In another aspect, the present disclosure provides a use of the compounds described herein for treating, preventing, or ameliorating a chronic pain condition.

The present disclosure further provides a method of treating or ameliorating chronic pain, comprising administering to a subject in need thereof a therapeutically effective amount of a compound described herein. A subject includes, but not limited to, a human or an animal. In certain embodiments, the pain includes chronic pain (which includes but is not limited to, neuropathic pain, postoperative pain, and inflammatory pain), and surgical pain.

In one aspect, the present disclosure provides a method of activating TAAR1 comprising administering to a subject in need thereof an effective amount of a compound described herein. In some embodiments, the compound is a TAAR1 agonist or partial agonist.

In another aspect, the present disclosure provides a pharmaceutical composition comprising a therapeutically effective amount of a compound described herein and one or more pharmaceutically acceptable carriers. Such compositions are useful for treating, preventing, or ameliorating pain in a patient.

In another aspect, the present disclosure provides a compound described herein for use in treatment, or amelioration of pain in a patient in need of said treatment or amelioration.

The present disclosure further relates to a kit, comprising a container containing an effective amount of a compound described herein and instructions for therapeutic use.

A further aspect of the present disclosure is to provide a method of making a compound described herein.

In another aspect, the present disclosure provides a compound described herein for use in treatment, or amelioration of pain in a patient in need thereof, such as acute pain, chronic pain (which includes but is not limited to, neuropathic pain, postoperative pain, and inflammatory pain), or surgical pain. In one embodiment, the compound is for the treatment or amelioration of neuropathic pain in the patient.

In another aspect, the present disclosure provides a compound described herein for use as a medicament.

In another aspect, the present disclosure provides use of a compound described herein in the manufacture of a medicament for treating, or ameliorating pain in a patient, such as acute pain, chronic pain, or surgical pain. One embodiment provides use of a compound described herein in the manufacture of a medicament for the treatment or amelioration of neuropathic pain.

The present disclosure further provides methods for preparing a pharmaceutical composition, comprising admixing a compound described herein and a pharmaceutically acceptable carrier to form the pharmaceutical composition.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

BRIEF DESCRIPTION OF THE DRAWINGS/FIGURES

FIG. 1 depicts the effect of compound (8) on SNL-induced mechanical hyperalgesia in rats.

DETAILED DESCRIPTION OF THE INVENTION

The present disclosure provides pseudodimers of 2-aminoxazoline compounds, including mono- and hetero-pseudodimers.

In one aspect, the present disclosure relates to a compound of Formula (I):

I

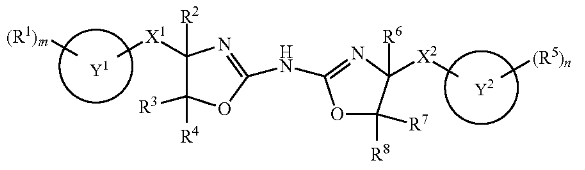

or a pharmaceutically acceptable salt or solvate thereof, wherein each $R^1$ and each $R^5$ are independently:
deuterium,
tritium,
lower alkyl,
lower alkoxy,
lower alkyl substituted by one or more same or different halogens,
lower alkoxy substituted by one or more same or different halogens,
halogen,
phenyl unsubstituted or substituted by one or more same or different halogens,
phenyloxy,
benzyl,
benzyloxy,
COO-lower alkyl,
—O—$(CH_2)_o$—O-lower alkyl,
—NH-cycloalkyl,
cycloalkyl,
piperidin-1-yl, or
tetrahydropyran-4-yloxy;

$X^1$ and $X^2$ are each independently a bond, —$CH(R^{20})$—, —$CH(R^{20})CH(R^{21})$—, —$OCH(R^{20})$—, —$N(R^{20})CH(R^{21})$—, —$CH_2OCH(R^{20})$—, —$CH_2CH_2CH_2$—, —$SCH(R^{20})$—, —$S(O)_2CH(R^{20})$—, —$CH_2SCH_2$—, —$CH_2N(R^{20})CH_2$—, -cycloalkyl-$CH_2$— or —$Si(R^{20})(R^{21})CH_2$—, wherein $R^{20}$ and $R^{21}$ are each independently hydrogen, lower alkyl, lower alkyl substituted by one or more same or different halogens, or benzyl unsubstituted or substituted by one or more same or different substituents selected from the group consisting of alkoxy and halogen;

$R^2$ and $R^6$ are each independently hydrogen, phenyl or lower alkyl;

$R^3$, $R^4$, $R^7$, and $R^8$ are each independently hydrogen, lower alkyl, lower alkoxy, or lower alkyl substituted by one or more same or different halogens, or lower alkoxy substituted by one or more same or different halogens;

$Y^1$ and $Y^2$ are each independently phenyl, naphthyl, thiophenyl, pyridinyl, cycloalkyl, 1,2,3,4-tetrahydro-naphthalen-2-yl, 2,3-dihydrobenzo[1,4]dioxin-6-yl, benzo[1,3]dioxol-5-yl, pyrimidyl, indanyl, 2,3-dihydroindol-1-yl, or 3,4-dihydro-quinolin-1-yl;

m and n are each independently 0, 1, 2 or 3; and o is 1, 2, or 3.

In one embodiment, the two oxazoline moieties in the compounds of Formula (I) disclosed herein,

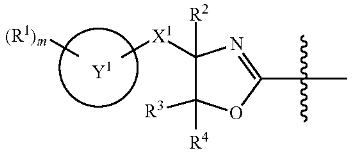

and

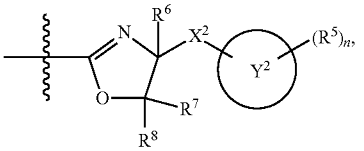

are the same. Such compounds sometimes are referred to as mono-pseudo dimers.

In another embodiment, the two oxazoline moieties in the compounds of Formula (I) disclosed herein,

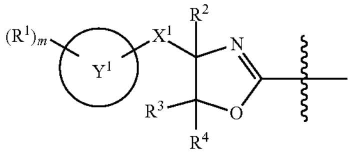

and

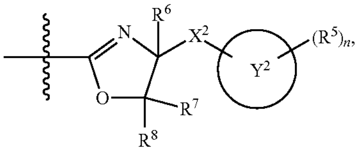

are different. Such compounds are referred to as hetero-pseudo dimers.

Some of the compounds disclosed herein may contain one or more asymmetric centers and may thus give rise to enantiomers, diastereomers, and other stereoisomeric forms. The invention is meant to encompass the compounds in all such possible forms, as well as their racemic and resolved forms and mixtures thereof. Further, individual diastereomers and enantiomers of a compound of the invention may be separated according to methods known to those of ordinary skill in the art in view of the present disclosure.

All tautomers of the compounds are intended to be encompassed by the invention as well.

In some embodiments, the present disclosure provides a compound of Formula (I), or a pharmaceutically acceptable salt or solvate thereof, wherein $X^1$ and $X^2$ are each independently a bond, $—CH(R^{20})—$, $—CH(R^{20})CH(R^{21})—$, $—OCH_2—$, $—CH_2OCH(R^{20})—$, $—N(R^{20})CH(R^{21})—$, wherein $R^{20}$ and $R^{21}$ are each independently hydrogen, lower alkyl, or lower alkyl substituted by one or more same or different halogens.

In some embodiments, the present disclosure provides a compound of Formula (I), or a pharmaceutically acceptable salt or solvate thereof, wherein $Y^1$ and $Y^2$ are each independently phenyl, naphthyl, thiophenyl, pyridinyl, cycloalkyl, 1,2,3,4-tetrahydro-naphthalen-2-yl, 2,3-dihydrobenzo[1,4]dioxin-6-yl, or benzo[1,3]dioxol-5-yl.

In some embodiments, the present disclosure provides a compound of Formula (I), or a pharmaceutically acceptable salt or solvate thereof, wherein $X^1$ and $X^2$ are each independently a bond, $—CH(R^{20})CH(R^{21})—$, or $—N(R^{20})CH(R^{21})—$; and $Y^1$ and $Y^2$ are phenyl.

In some embodiments, the present disclosure provides a compound of Formula (I), or a pharmaceutically acceptable salt or solvate thereof, wherein each $R^1$ and each $R^5$ are independently:

lower alkyl, lower alkoxy, lower alkyl substituted by one or more same or different halogens, lower alkoxy substituted by one or more same or different halogens, or halogen;

$R^2$ and $R^6$ are each independently hydrogen, phenyl, or lower alkyl; and $R^3$, $R^4$, $R^7$, and $R^8$ are hydrogen.

In some embodiments, the present disclosure provides a compound of Formula (I), or a pharmaceutically acceptable salt or solvate thereof, wherein each $R^1$ and each $R^5$ are independently:

lower alkyl, lower alkoxy, lower alkyl substituted by one or more same or different halogens, lower alkoxy substituted by one or more same or different halogens, or halogen;

$R^2$ and $R^6$ are hydrogen;

$R^3$ and $R^7$ are each independently lower alkyl, or lower alkyl substituted by one or more same or different halogens; and $R^4$ and $R^8$ are each independently hydrogen, lower alkyl, or lower alkyl substituted by one or more same or different halogens;

In some embodiments, the present disclosure provides a compound of Formula (I), or a pharmaceutically acceptable salt or solvate thereof, wherein each $R^1$ and each $R^5$ are independently halogen; and $R^2$, $R^3$, $R^4$, $R^6$, $R^7$, and $R^8$ are hydrogen;

Mono-Pseudodimers

In some embodiments, the present disclosure provides pseudodimers containing two oxazoline moieties linked by a nitrogen atom, having Formula (II):

II

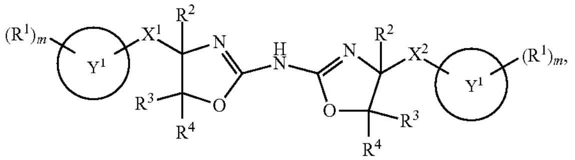

or a pharmaceutically acceptable salt or solvate thereof, wherein each $R^1$ is independently:

deuterium, tritium, lower alkyl, lower alkoxy, lower alkyl substituted by one or more same or different halogens,
lower alkoxy substituted by one or more same or different halogens,
halogen,
phenyl unsubstituted or substituted by one or more same or different halogens,
phenyloxy,
benzyl,
benzyloxy,
COO-lower alkyl,
—O—$(CH_2)_o$—O-lower alkyl,
—NH-cycloalkyl,
cycloalkyl,
piperidin-1-yl, or
tetrahydropyran-4-yloxy;

$X^1$ is a bond, —$CH(R^{20})$—, —$CH(R^{20})CH(R^{21})$—, —$OCH(R^{20})$—, —$N(R^{20})CH(R^{21})$—, —$CH_2OCH(R^{20})$—, —$CH_2CH_2CH_2$—, —$SCH(R^{20})$—, —$S(O)_2CH(R^{20})$—, —$CH_2SCH_2$—, —$CH_2N(R^{20})CH_2$—, -cycloalkyl-$CH_2$—, or —$Si(R^{20})(R^{21})CH_2$—, wherein $R^{20}$ and $R^{21}$ are each independently hydrogen, lower alkyl, lower alkyl substituted by one or more same or different halogens, or benzyl unsubstituted or substituted by one or more same or different substituents selected from the group consisting of alkoxy or halogen;

$R^2$ is hydrogen, phenyl or lower alkyl;

$R^3$ and $R^4$ are each independently hydrogen, lower alkyl, or lower alkyl substituted by one or more same or different halogens;

$Y^1$ is phenyl, naphthyl, thiophenyl, pyridinyl, cycloalkyl, 1,2,3,4-tetrahydro-naphthalen-2-yl, 2,3-dihydrobenzo[1,4]dioxin-6-yl, benzo[1,3]dioxol-5-yl, pyrimidyl, indanyl, 2,3-dihydroindol-1-yl, or 3,4-dihydro-quinolin-1-yl;

m is 0, 1, 2 or 3; and o is 1, 2, or 3.

In some embodiments, the compounds of Formula (II) contains two identical oxazoline moieties. In other embodiments, the compounds of Formula (II) contains two different oxazoline moieties.

In some embodiments, the present disclosure provides a compound of Formula (II), or a pharmaceutically acceptable salt or solvate thereof, wherein $X^1$ is a bond, —$CH(R^{20})$—, —$CH(R^{20})CH(R^{21})$—, —$OCH_2$—, —$CH_2OCH(R^{20})$—, —$N(R^{20})CH(R^{21})$—, wherein $R^{20}$ and $R^{21}$ are each independently hydrogen, lower alkyl, or lower alkyl substituted by one or more same or different halogens.

In some embodiments, the present disclosure provides a compound of Formula (II), or a pharmaceutically acceptable salt or solvate thereof, wherein $Y^1$ is phenyl, naphthyl, thiophenyl, pyridinyl, cycloalkyl, 1,2,3,4-tetrahydro-naphthalen-2-yl, 2,3-dihydrobenzo[1,4]dioxin-6-yl, or benzo[1,3]dioxol-5-yl.

In some embodiments, the present disclosure provides a compound of Formula (II), or a pharmaceutically acceptable salt or solvate thereof, wherein $X^1$ is a bond, —$CH(R^{20})CH(R^{21})$—, or —$N(R^{20})CH(R^{21})$—; and $Y^1$ is phenyl.

In some embodiments, the present disclosure provides a compound of Formula (II), or a pharmaceutically acceptable salt or solvate thereof, wherein each $R^1$ is independently:
lower alkyl,
lower alkoxy,
lower alkyl substituted by one or more same or different halogens,
lower alkoxy substituted by one or more same or different halogens, or
halogen;

$R^2$ is hydrogen, phenyl, or lower alkyl; and $R^3$ and $R^4$ are hydrogen.

In some embodiments, the present disclosure provides a compound of Formula (II), or a pharmaceutically acceptable salt or solvate thereof, wherein each $R^1$ is:
lower alkyl,
lower alkoxy,
lower alkyl substituted by one or more same or different halogens,
lower alkoxy substituted by one or more same or different halogens, or
halogen;

$R^2$ is hydrogen; $R^3$ is lower alkyl, or lower alkyl substituted by one or more same or different halogens; and $R^4$ is hydrogen, lower alkyl, or lower alkyl substituted by one or more same or different halogens.

In some embodiments, the present disclosure provides a compound of Formula (II), or a pharmaceutically acceptable salt or solvate thereof, wherein each $R^1$ is independently halogen; and all of $R^2$, $R^3$, and $R^4$ are hydrogen.

In some embodiments, the compound of Formula (II) is a compound of Formula (II-A):

II-A

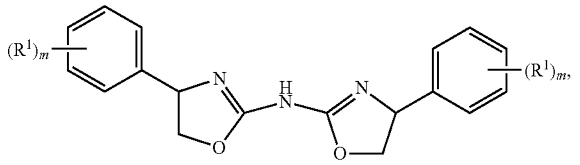

or a pharmaceutically acceptable salt or solvate thereof, wherein each $R^1$ is independently:
deuterium,
tritium,
lower alkyl,
lower alkoxy,
lower alkyl substituted by one or more same or different halogens,
lower alkoxy substituted by one or more same or different halogens,
halogen,
phenyl unsubstituted or substituted by one or more same or different halogens,
phenyloxy,
benzyl,
benzyloxy,
COO-lower alkyl,
—O—$(CH_2)_o$—O-lower alkyl,
—NH-cycloalkyl,
cycloalkyl,
piperidin-1-yl, or
tetrahydropyran-4-yloxy;

m is 0, 1, 2 or 3.

In some embodiments, the compound of Formula (II-A) is a compound of Formula (II-Aa):

II-Aa

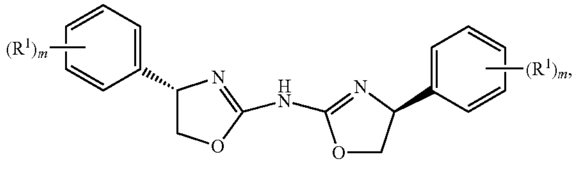

or a pharmaceutically acceptable salt or solvate thereof.

In some embodiments, the compound of Formula (II-A) is a compound of Formula (II-Ab):

II-Ab

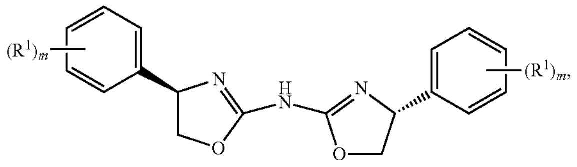

or a pharmaceutically acceptable salt or solvate thereof.

In some embodiments, the compound of Formula (II-A) is a compound of Formula (II-Ac):

II-Ac

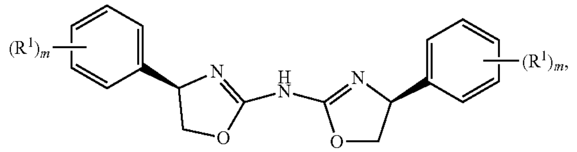

or a pharmaceutically acceptable salt or solvate thereof.

In some embodiments, the compound of Formula (II-A) is a compound of Formula (II-Ad):

II-Ad

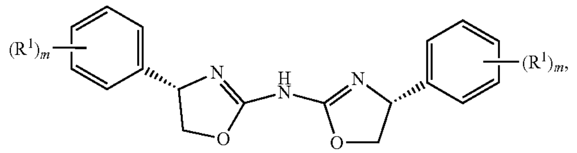

or a pharmaceutically acceptable salt or solvate thereof.

In some embodiments, the compound of Formula (II) is a compound of Formula (II-B):

II-B

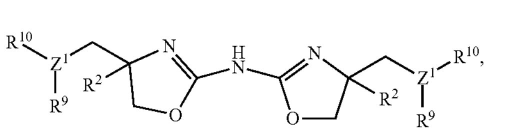

or a pharmaceutically acceptable salt or solvate thereof, wherein:

$Z^1$ is N or CH;

$R^2$ is hydrogen or lower alkyl;

$R^9$ is hydrogen, lower alkyl, or benzyl unsubstituted or substituted by one or more same or different substituents selected from the group consisting of alkoxy or halogen;

$R^{10}$ is aryl, wherein the aryl group is selected from the group consisting of phenyl, naphthyl, 1,2,3,4-tetrahydro-naphthalen-2-yl, and indanyl, and wherein the aryl group is unsubstituted or substituted by one to three substituents, selected from the group consisting of cycloalkyl, phenyl, phenyloxy, benzyl, benzyloxy, halogen, lower alkyl, lower alkoxy, piperidin-1-yl, lower alkyl substituted by one or more same or different halogens, and lower alkoxy substituted one or more same or different halogens; or $R^9$ and $R^{10}$, together with the N-atom to which they are attached, form an 8- to 10-membered heterocyclic group.

In some embodiments, $R^9$ and $R^{10}$ in formula (II-B), together with the N-atom to which they are attached, form an 8- to 10-membered heterocyclic group, e.g., but not limited to, 2,3-dihydroindol-1-yl and 3,4-dihydro-quinolin-1-yl.

In some embodiments, the compound of Formula (II-B) is a compound of Formula (II-Ba):

II-Ba

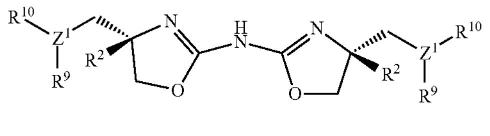

or a pharmaceutically acceptable salt or solvate thereof.

In some embodiments, the compound of Formula (II-B) is a compound of Formula (II-Bb):

II-Bb

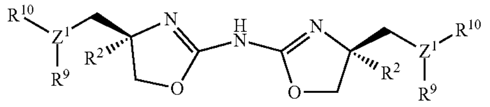

or a pharmaceutically acceptable salt or solvate thereof.

In some embodiments, the compound of Formula (II-B) is a compound of Formula (II-Bc):

II-Bc

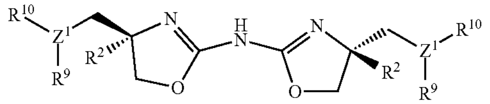

or a pharmaceutically acceptable salt or solvate thereof.

In some embodiments, the compound of Formula (II-B) is a compound of Formula (II-Bd):

II-Bd

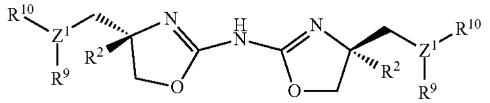

or a pharmaceutically acceptable salt or solvate thereof.

In certain embodiments, compounds of the present disclosure include, for example:

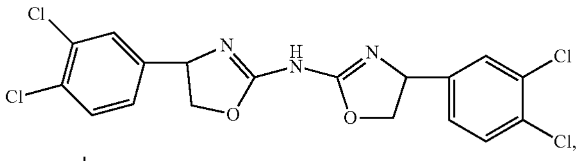

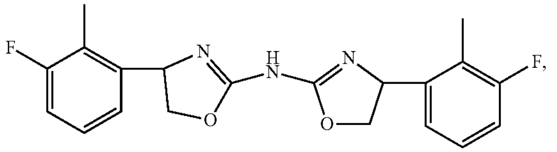

-continued
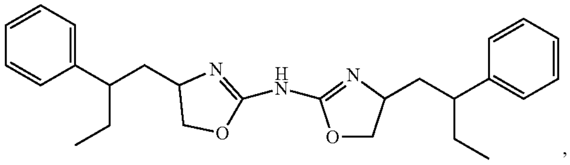
,
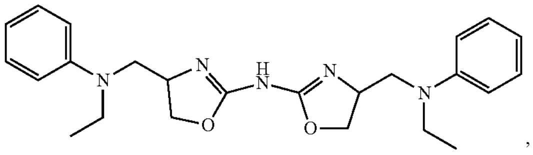
, and
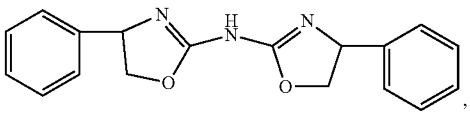
,
or pharmaceutically acceptable salts or solvates thereof.
In certain embodiments, compounds of the present disclosure include, for example:
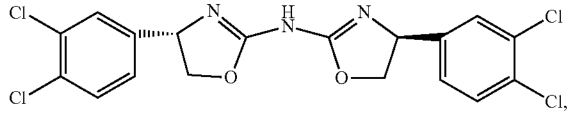
-continued
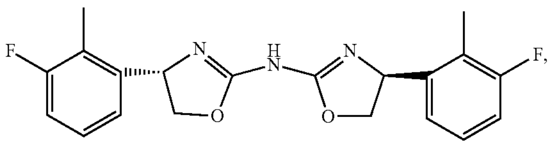
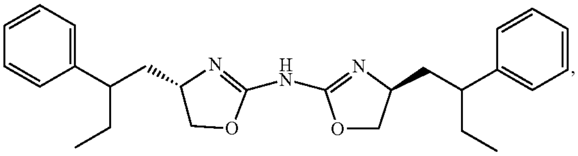
,
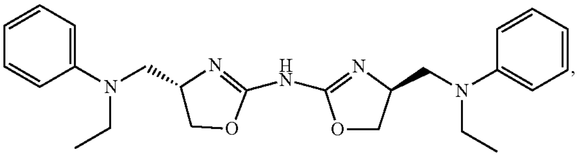
,
and
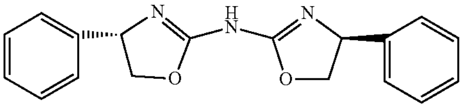
,
or pharmaceutically acceptable salts or solvates thereof.
Compounds of the present disclosure also include the following compounds:
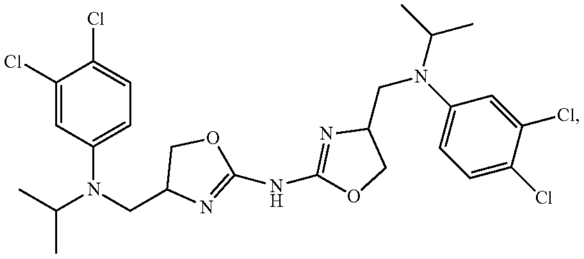
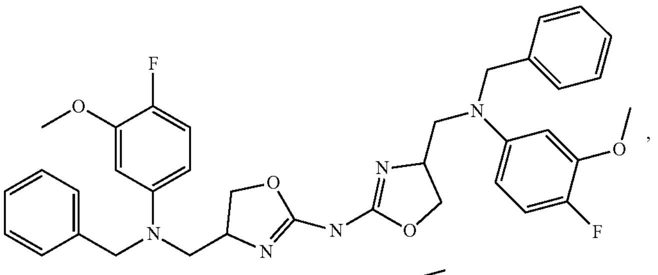
,
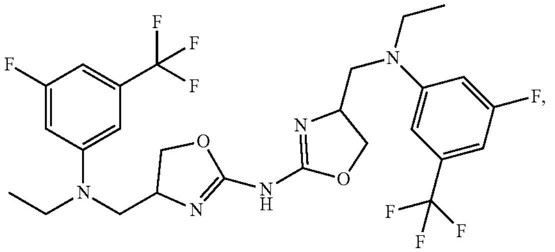

-continued
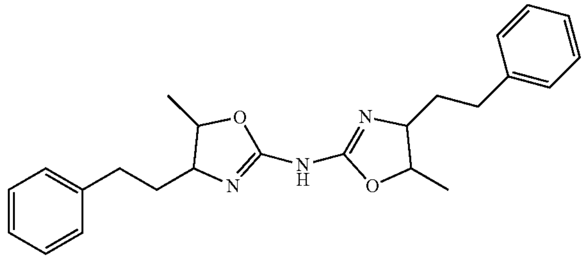,
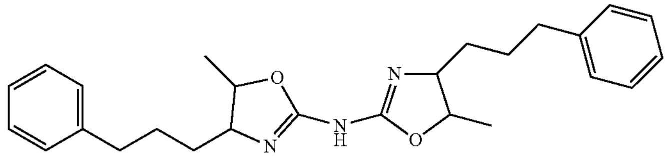,
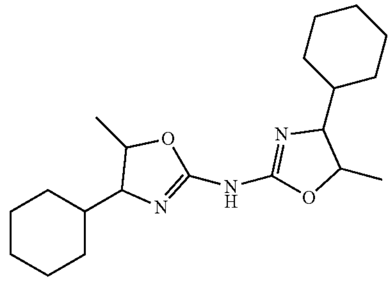,
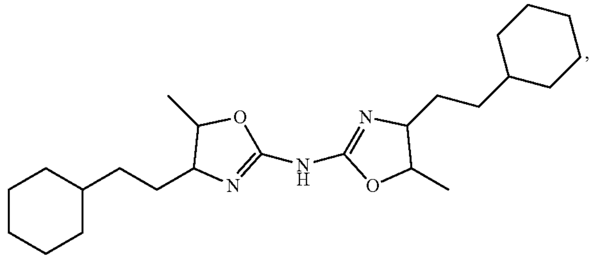,
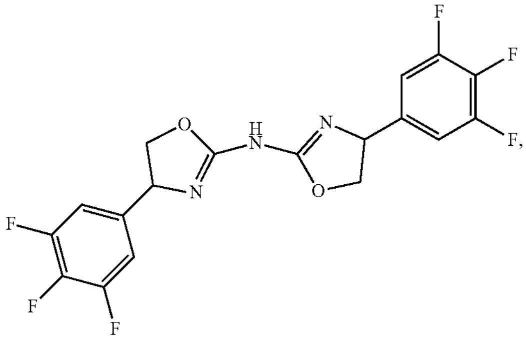,
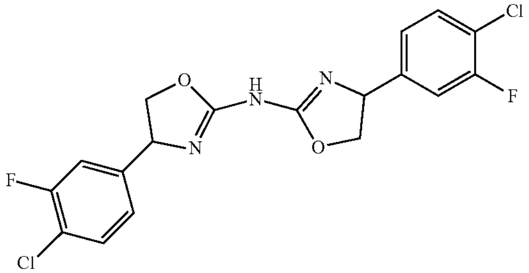,
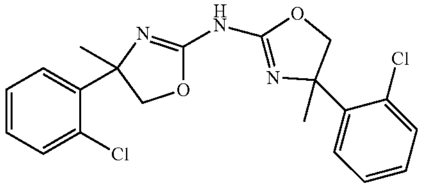,
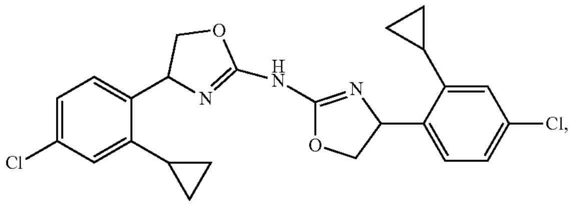,
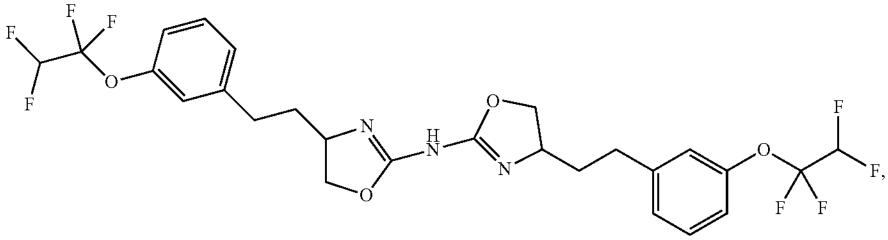, -continued
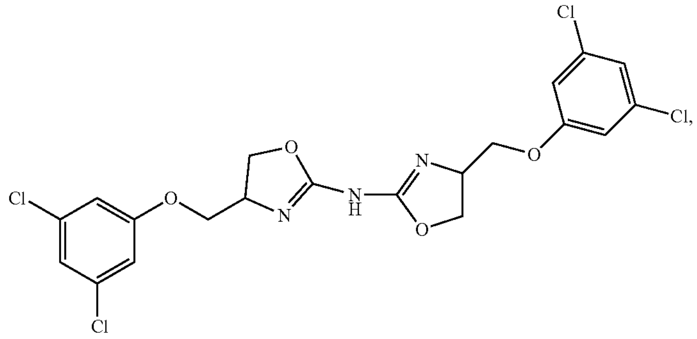
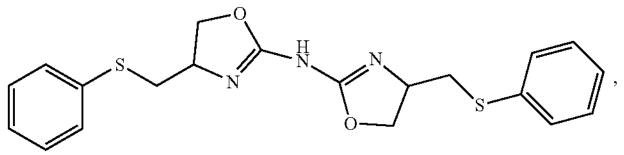
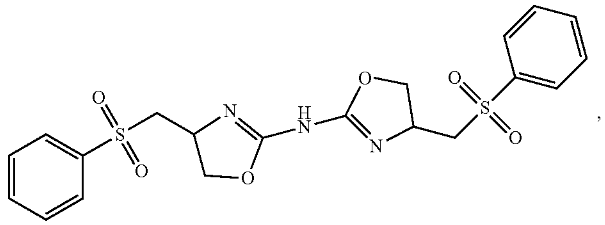
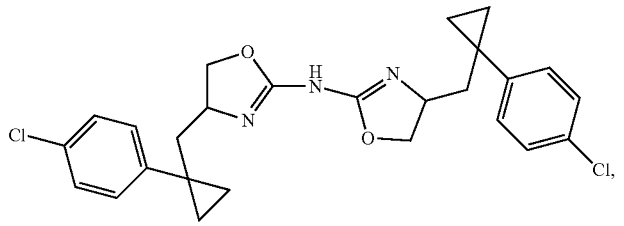
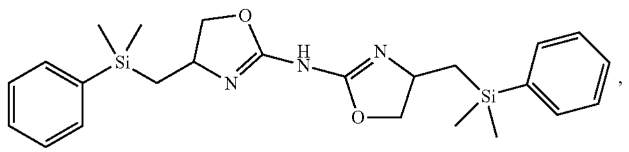
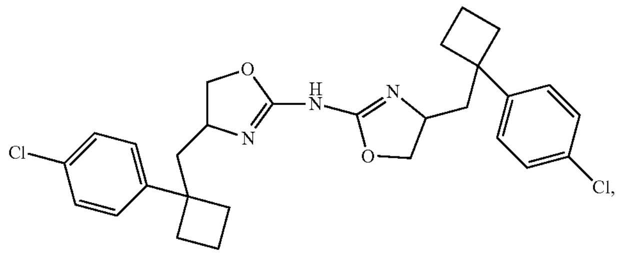
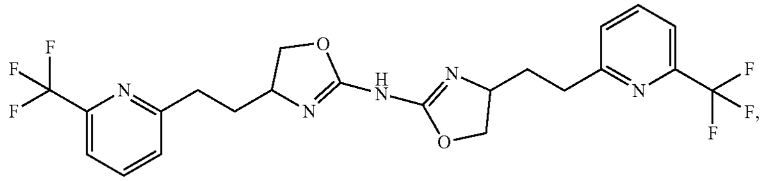
and -continued

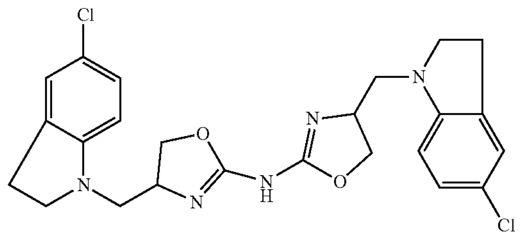

or pharmaceutically acceptable salts or solvates thereof.

The oxazoline moieties that can be used to construct the compounds of the present disclosure include, but are not limited to, the following structures:

4-[(ethyl-phenyl-amino)-methyl]-4,5-dihydro-oxazol-2-yl,
4-[(methyl-phenyl-amino)-methyl]-4,5-dihydro-oxazol-2-yl,
4-{[(3,4-dichloro-phenyl)-methyl-amino]-methyl}-4,5-dihydro-oxazol-2-yl,
4-{[(4-chloro-phenyl)-ethyl-amino]-methyl}-4,5-dihydro-oxazol-2-yl,
4-{[(3,4-dichloro-phenyl)-isopropyl-amino]-methyl}-4,5-dihydro-oxazol-2-yl,
4-{[(4-bromo-phenyl)-methyl-amino]-methyl}-4,5-dihydro-oxazol-2-yl,
4-{[(4-bromo-phenyl)-ethyl-amino]-methyl}-4,5-dihydro-oxazol-2-yl,
4-{[(3,4-dichloro-phenyl)-ethyl-amino]-methyl}-4,5-dihydro-oxazol-2-yl,
4-{[(3-bromo-phenyl)-methyl-amino]-methyl}-4,5-dihydro-oxazol-2-yl,
4-{[(3-bromo-phenyl)-ethyl-amino]-methyl}-4,5-dihydro-oxazol-2-yl,
4-{[(3-chloro-phenyl)-ethyl-amino]-methyl}-4,5-dihydro-oxazol-2-yl,
4-{[(4-chloro-2-fluoro-phenyl)-ethyl-amino]-methyl}-4,5-dihydro-oxazol-2-yl,
4-{[(4-chloro-2-fluoro-phenyl)-methyl-amino]-methyl}-4,5-dihydro-oxazol-2-yl,
4-{[ethyl-(2-fluoro-phenyl)-amino]-methyl}-4,5-dihydro-oxazol-2-yl,
4-{[(2-chloro-phenyl)-ethyl-amino]-methyl}-4,5-dihydro-oxazol-2-yl,
4-{[(4-chloro-phenyl)-methyl-amino]-methyl}-4,5-dihydro-oxazol-2-yl,
4-{[(4-chloro-phenyl)-ethyl-amino]-methyl}-4,5-dihydro-oxazol-2-yl,
4-{[(4-fluoro-phenyl)-methyl-amino]-methyl}-4,5-dihydro-oxazol-2-yl,
4-{[(4-chloro-phenyl)-isopropyl-amino]-methyl}-4,5-dihydro-oxazol-2-yl,
4-{[(2,4-difluoro-phenyl)-ethyl-amino]-methyl}-4,5-dihydro-oxazol-2-yl,
4-{[(2,4-difluoro-phenyl)-methyl-amino]-methyl}-4,5-dihydro-oxazol-2-yl,
4-{[(3,5-dichloro-phenyl)-methyl-amino]-methyl}-4,5-dihydro-oxazol-2-yl,
4-{[(3,5-dichloro-phenyl)-ethyl-amino]-methyl}-4,5-dihydro-oxazol-2-yl,
4-[(3-chloro-phenylamino)-methyl]-4,5-dihydro-oxazol-2-yl,
4-[(2-chloro-phenylamino)-methyl]-4,5-dihydro-oxazol-2-yl,
4-[(4-trifluoromethyl-phenylamino)-methyl]-4,5-dihydro-oxazol-2-yl,
4-[(2,4-difluoro-phenylamino)-methyl]-4,5-dihydro-oxazol-2-yl,
4-[(2-fluoro-4-methyl-phenylamino)-methyl]-4,5-dihydro-oxazol-2-yl,
4-{[ethyl-(4-trifluoromethyl-phenyl)-amino]-methyl}-4,5-dihydro-oxazol-2-yl,
4-{[methyl-(4-trifluoromethyl-phenyl)-amino]-methyl}-4,5-dihydro-oxazol-2-yl,
4-{[ethyl-(2-methyl-4-trifluoromethyl-phenyl)-amino]-methyl}-4,5-dihydro-oxazol-2-yl,
(2-amino-4,5-dihydro-oxazol-4-ylmethyl)-(6-chloro-pyridin-2-yl),
4-{[(4-chloro-3-methoxy-phenyl)-methyl-amino]-methyl}-4,5-dihydro-oxazol-2-yl,
4-{[(4-chloro-3-methoxy-phenyl)-ethyl-amino]-methyl}-4,5-dihydro-oxazol-2-yl,
4-{[(4-fluoro-3-methoxy-phenyl)-methyl-amino]-methyl}-4,5-dihydro-oxazol-2-yl,
4-{[ethyl-(4-fluoro-3-methoxy-phenyl)-amino]-methyl}-4,5-dihydro-oxazol-2-yl,
4-{[benzyl-(4-fluoro-3-methoxy-phenyl)-amino]-methyl}-4,5-dihydro-oxazol-2-yl,
4-{[benzyl-(4-fluoro-phenyl)-amino]-methyl}-4,5-dihydro-oxazol-2-yl,
4-{[benzyl-(4-chloro-phenyl)-amino]-methyl}-4,5-dihydro-oxazol-2-yl,
4-[(ethyl-m-tolyl-amino)-methyl]-4,5-dihydro-oxazol-2-yl,
4-{[ethyl-(3-ethyl-phenyl)-amino]-methyl}-4,5-dihydro-oxazol-2-yl,
4-{[ethyl-(4-ethyl-phenyl)-amino]-methyl}-4,5-dihydro-oxazol-2-yl,
4-[(methyl-naphthalen-2-yl-amino)-methyl]-4,5-dihydro-oxazol-2-yl,
4-[(ethyl-naphthalen-2-yl-amino)-methyl]-4,5-dihydro-oxazol-2-yl,
4-{[ethyl-(3-fluoro-5-trifluoromethyl-phenyl)-amino]-methyl}-4,5-dihydro-oxazol-2-yl,
4-[(3-fluoro-4-trifluoromethyl-phenylamino)-methyl]-4,5-dihydro-oxazol-2-yl,
4-[(ethyl-indan-5-yl-amino)-methyl]-4,5-dihydro-oxazol-2-yl,
4-{[methyl-(3-oxazol-5-yl-phenyl)-amino]-methyl}-4,5-dihydro-oxazol-2-yl, and
4-{[ethyl-(3-oxazol-5-yl-phenyl)-amino]-methyl}-4,5-dihydro-oxazol-2-yl.
5-methyl-4-phenethyl-4,5-dihydro-oxazol-2-yl;
5-ethyl-4-phenethyl-4,5-dihydro-oxazol-2-yl;
5-methyl-4-(3-phenyl-propyl)-4,5-dihydro-oxazol-2-yl;
4-benzyl-5-methyl-4,5-dihydro-oxazol-2-yl;
4-[2-(4-chloro-phenyl)-ethyl]-5-methyl-4,5-dihydro-oxazol-2-yl;

4-[2-(3,4-dichloro-phenyl)-ethyl]-5-methyl-4,5-dihydro-oxazol-2-yl;
4-[3-(4-chloro-phenyl)-propyl]-5-methyl-4,5-dihydro-oxazol-2-yl;
4-cyclohexyl-5-methyl-4,5-dihydro-oxazol-2-yl;
4-(2-cyclohexyl-ethyl)-5-methyl-4,5-dihydro-oxazol-2-yl;
4-(2-chloro-phenyl)-4,5-dihydro-oxazol-2-yl,
4-(4-chloro-phenyl)-4,5-dihydro-oxazol-2-yl,
4-(2,4-difluoro-phenyl)-4,5-dihydro-oxazol-2-yl,
4-(2,3-difluoro-phenyl)-4,5-dihydro-oxazol-2-yl,
4-(3,4-dichlorophenyl)-4,5-dihydro-oxazol-2-yl,
4-(2,5-difluoro-phenyl)-4,5-dihydro-oxazol-2-yl,
4-(2,3,4-trifluoro-phenyl)-4,5-dihydro-oxazol-2-yl,
4-(3-chloro-2-fluoro-phenyl)-4,5-dihydro-oxazol-2-yl,
4-(5-chloro-2-fluoro-phenyl)-4,5-dihydro-oxazol-2-yl,
4-(3-bromo-2,4-difluoro-phenyl)-4,5-dihydro-oxazol-2-yl,
4-(2,4-difluoro-phenyl)-4,5-dihydro-oxazol-2-yl,
4-(3,4-dichloro-phenyl)-4,5-dihydro-oxazol-2-yl,
4-(2,5-difluoro-phenyl)-4,5-dihydro-oxazol-2-yl,
4-(2,4,5-trifluoro-phenyl)-4,5-dihydro-oxazol-2-yl,
4-(3-chloro-2-fluoro-phenyl)-4,5-dihydro-oxazol-2-yl,
4-(2,3,5-trifluoro-phenyl)-4,5-dihydro-oxazol-2-yl,
4-(3,4-dichloro-phenyl)-4-methyl-4,5-dihydro-oxazol-2-yl,
4-(4-chloro-phenyl)-4-methyl-4,5-dihydro-oxazol-2-yl,
4-(3,4-difluoro-phenyl)-4,5-dihydro-oxazol-2-yl,
4-(2,3-dichloro-phenyl)-4,5-dihydro-oxazol-2-yl,
4-(4-chloro-phenyl)-4,5-dihydro-oxazol-2-yl,
4-(3,4,5-trifluoro-phenyl)-4,5-dihydro-oxazol-2-yl,
4-(3-chloro-4-fluoro-phenyl)-4,5-dihydro-oxazol-2-yl,
4-(4-chloro-3-fluoro-phenyl)-4,5-dihydro-oxazol-2-yl,
4-(3,5-difluoro-phenyl)-4,5-dihydro-oxazol-2-yl,
4-(3-chloro-5-fluoro-phenyl)-4,5-dihydro-oxazol-2-yl,
4-(2-chloro-phenyl)-4-methyl-4,5-dihydro-oxazol-2-yl,
4-(3-chloro-phenyl)-4,5-dihydro-oxazol-2-yl,
4-(3-bromo-phenyl)-4,5-dihydro-oxazol-2-yl,
4-(2,5-difluoro-phenyl)-4-methyl-4,5-dihydro-oxazol-2-yl,
4-(3,5-dichloro-phenyl)-4,5-dihydro-oxazol-2-yl,
4-(5-chloro-2-fluoro-phenyl)-4,5-dihydro-oxazol-2-yl,
4-(3-chloro-phenyl)-4,5-dihydro-oxazol-2-yl,
4-(2-fluoro-phenyl)-4-methyl-4,5-dihydro-oxazol-2-yl,
4-(3-bromo-phenyl)-4,5-dihydro-oxazol-2-yl,
4-(3-fluoro-phenyl)-4,5-dihydro-oxazol-2-yl,
4-(3,5-dichloro-phenyl)-4,5-dihydro-oxazol-2-yl,
4-(2,4-difluoro-phenyl)-4-methyl-4,5-dihydro-oxazol-2-yl,
4-methyl-4-(2,3,5-trifluoro-phenyl)-4,5-dihydro-oxazol-2-yl,
4-(4-bromo-phenyl)-4-methyl-4,5-dihydro-oxazol-2-yl,
4-(2,4-dichloro-phenyl)-4,5-dihydro-oxazol-2-yl,
4-(4-chloro-3-fluoro-phenyl)-4-methyl-4,5-dihydro-oxazol-2-yl,
4-(2-bromo-phenyl)-4,5-dihydro-oxazol-2-yl,
4-methyl-4-(2,4,5-trifluoro-phenyl)-4,5-dihydro-oxazol-2-yl,
4-(4-bromo-3-fluoro-phenyl)-4,5-dihydro-oxazol-2-yl,
4-(2,5-dichloro-phenyl)-4,5-dihydro-oxazol-2-yl,
4-(2-bromo-phenyl)-4,5-dihydro-oxazol-2-yl,
4-(3-chloro-5-fluoro-phenyl)-4-methyl-4,5-dihydro-oxazol-2-yl,
4-methyl-4-(2,3,4-trifluoro-phenyl)-4,5-dihydro-oxazol-2-yl,
4-(5-chloro-2-fluoro-phenyl)-4-methyl-4,5-dihydro-oxazol-2-yl,
4-methyl-4-(4-chloro-2,5-difluoro-phenyl)-4,5-dihydro-oxazol-2-yl,
4-methyl-4-(3,4,5-trifluoro-phenyl)-4,5-dihydro-oxazol-2-yl,
4-(3-chloro-4-fluoro-phenyl)-4-methyl-4,5-dihydro-oxazol-2-yl,
4-(4-chloro-2,5-difluoro-phenyl)-4-methyl-4,5-dihydro-oxazol-2-yl,
4-(4-bromo-2-chloro-phenyl)-4,5-dihydro-oxazol-2-yl,
4-(2,4-dichloro-phenyl)-4-methyl-4,5-dihydro-oxazol-2-yl,
4-(2,4-dichloro-phenyl)-4,5-dihydro-oxazol-2-yl,
4-(2,5-dichloro-phenyl)-4,5-dihydro-oxazol-2-yl,
4-(2,5-dichloro-phenyl)-4-methyl-4,5-dihydro-oxazol-2-yl,
4-(2,3,4-trifluoro-phenyl)-4,5-dihydro-oxazol-2-yl,
4-methyl-4-(3,4,5-trifluoro-phenyl)-4,5-dihydro-oxazol-2-yl,
4-(3-chloro-2-fluoro-phenyl)-4-methyl-4,5-dihydro-oxazol-2-yl,
4-(4-chloro-phenyl)-4-ethyl-4,5-dihydro-oxazol-2-yl,
4-(4-bromo-2-chloro-phenyl)-4,5-dihydro-oxazol-2-yl,
4-(2-chloro-4-fluoro-phenyl)-4-methyl-4,5-dihydro-oxazol-2-yl,
4-(4-bromo-3-fluoro-phenyl)-4,5-dihydro-oxazol-2-yl,
4-(4-bromo-3-chloro-phenyl)-4,5-dihydro-oxazol-2-yl,
4-(3,4-dichloro-phenyl)-4-ethyl-4,5-dihydro-oxazol-2-yl,
4-(4-bromo-2-fluoro-phenyl)-4,5-dihydro-oxazol-2-yl,
4-(2-trifluoromethyl-phenyl)-4,5-dihydro-oxazol-2-yl,
4-o-tolyl-4,5-dihydro-oxazol-2-yl,
4-(4-trifluoromethoxy-phenyl)-4,5-dihydro-oxazol-2-yl,
4-(4-methoxy-3-methyl-phenyl)-4,5-dihydro-oxazol-2-yl,
4-(4-benzyloxy-phenyl)-4,5-dihydro-oxazol-2-yl,
4-(2-trifluoromethyl-phenyl)-4,5-dihydro-oxazol-2-yl,
4-(4-methoxy-3-methyl-phenyl)-4,5-dihydro-oxazol-2-yl,
4-methyl-4-(4-trifluoromethyl-phenyl)-4,5-dihydro-oxazol-2-yl,
4-(3-trifluoromethyl-phenyl)-4,5-dihydro-oxazol-2-yl,
4-methyl-4-p-tolyl-4,5-dihydro-oxazol-2-yl,
4-methyl-4-(3-trifluoromethyl-phenyl)-4,5-dihydro-oxazol-2-yl,
4-(4-methoxy-2-trifluoromethyl-phenyl)-4,5-dihydro-oxazol-2-yl,
4-biphenyl-4-yl-4,5-dihydro-oxazol-2-yl,
4-(4'-chloro-biphenyl-4-yl)-4,5-dihydro-oxazol-2-yl,
4-(3-chloro-4-methoxyphenyl)-4,5-dihydro-oxazol-2-yl,
4-(2-fluoro-4-trifluoromethyl-phenyl)-4-methyl-4,5-dihydro-oxazol-2-yl,
4-(4-fluoro-2-trifluoromethyl-phenyl)-4,5-dihydro-oxazol-2-yl,
4-(5-chloro-2-trifluoromethyl-phenyl)-4,5-dihydro-oxazol-2-yl,
4-(4-chloro-2-trifluoromethyl-phenyl)-4,5-dihydro-oxazol-2-yl,
4-(4,5-dichloro-2-trifluoromethyl-phenyl)-4,5-dihydro-oxazol-2-yl,
4-(5-fluoro-2-trifluoromethyl-phenyl)-4,5-dihydro-oxazol-2-yl,
4-(5-fluoro-2-methyl-phenyl)-4,5-dihydro-oxazol-2-yl,
4-(4-chloro-3-methyl-phenyl)-4-methyl-4,5-dihydro-oxazol-2-yl,
4-(5-chloro-2-methyl-phenyl)-4,5-dihydro-oxazol-2-yl,
4-(4-chloro-2-fluoro-5-methyl-phenyl)-4-methyl-4,5-dihydro-oxazol-2-yl,
4-(4-bromo-2-trifluoromethyl-phenyl)-4,5-dihydro-oxazol-2-yl,
4-(4-fluoro-2-methyl-phenyl)-4,5-dihydro-oxazol-2-yl,
4-(4-chloro-2-ethyl-phenyl)-4,5-dihydro-oxazol-2-yl,
4-(3-chloro-4-methyl-phenyl)-4,5-dihydro-oxazol-2-yl,
4-(4-chloro-2-cyclopropyl-phenyl)-4,5-dihydro-oxazol-2-yl,
4-(3-fluoro-2-methyl-phenyl)-4,5-dihydro-oxazol-2-yl, 4-(3-fluoro-2-trifluoromethyl-phenyl)-4,5-dihydro-oxazol-2-yl,
4-(2-chloro-benzyl)-4,5-dihydro-oxazol-2-yl,
4-(3-trifluoromethyl-benzyl)-4,5-dihydro-oxazol-2-yl,
4-(2-fluoro-5-methyl-benzyl)-4,5-dihydro-oxazol-2-yl,
4-phenethyl-4,5-dihydro-oxazol-2-yl,
4-methyl-4-phenethyl-4,5-dihydro-oxazol-2-yl,
4-[2-(4-fluoro-phenyl)-ethyl]-4,5-dihydro-oxazol-2-yl,
4-[2-(4-fluoro-3-methoxy-phenyl)-ethyl]-4,5-dihydro-oxazol-2-yl,
4-[2-(2,4-difluoro-phenyl)-ethyl]-4,5-dihydro-oxazol-2-yl,
4-[2-(3,4-difluoro-phenyl)-ethyl]-4,5-dihydro-oxazol-2-yl,
4-[2-(2-trifluoromethyl-phenyl)-ethyl]-4,5-dihydro-oxazol-2-yl,
4-[2-(2-fluoro-phenyl)-ethyl]-4,5-dihydro-oxazol-2-yl,
4-[2-(3-fluoro-phenyl)-ethyl]-4,5-dihydro-oxazol-2-yl,
4-[2-(3,5-difluoro-phenyl)-ethyl]-4,5-dihydro-oxazol-2-yl,
4-(2-o-tolyl-ethyl)-4,5-dihydro-oxazol-2-yl,
4-(2-m-tolyl-ethyl)-4,5-dihydro-oxazol-2-yl,
4-(2-p-tolyl-ethyl)-4,5-dihydro-oxazol-2-yl,
4-[2-(4-trifluoromethyl-phenyl)-ethyl]-4,5-dihydro-oxazol-2-yl,
4-[2-(3-trifluoromethyl-phenyl)-ethyl]-4,5-dihydro-oxazol-2-yl,
4-[2-(3,4-dichloro-phenyl)-ethyl]-4,5-dihydro-oxazol-2-yl,
4-[2-(4-chloro-2-fluoro-phenyl)-ethyl]-4,5-dihydro-oxazol-2-yl,
4-[2-(4-fluoro-3-trifluoromethyl-phenyl)-ethyl]-4,5-dihydro-oxazol-2-yl,
4-[2-(3-fluoro-4-trifluoromethyl-phenyl)-ethyl]-4,5-dihydro-oxazol-2-yl,
4-[2-(3,5-dichloro-phenyl)-ethyl]-4,5-dihydro-oxazol-2-yl,
4-[2-(2-chloro-4-fluoro-phenyl)-ethyl]-4,5-dihydro-oxazol-2-yl,
4-[2-(4-fluoro-3-methyl-phenyl)-ethyl]-4,5-dihydro-oxazol-2-yl,
4-{2-[3-(1,1,2,2-tetrafluoro-ethoxy)-phenyl]-ethyl}-4,5-dihydro-oxazol-2-yl,
4-[2-(2-fluoro-3-trifluoromethyl-phenyl)-ethyl]-4,5-dihydro-oxazol-2-yl,
4-[2-(3-bromo-phenyl)-ethyl]-4,5-dihydro-oxazol-2-yl,
4-[2-(4-chloro-3-trifluoromethyl-phenyl)-ethyl]-4,5-dihydro-oxazol-2-yl,
4-[2-(3-fluoro-4-trifluoromethoxy-phenyl)-ethyl]-4,5-dihydro-oxazol-2-yl,
4-[2-(4-fluoro-3-trifluoromethoxy-phenyl)-ethyl]-4,5-dihydro-oxazol-2-yl,
4-[2-(2,3-dichloro-phenyl)-ethyl]-4,5-dihydro-oxazol-2-yl,
4-[2-(3-chloro-4-trifluoromethoxy-phenyl)-ethyl]-4,5-dihydro-oxazol-2-yl,
4-[2-(2-chloro-3-trifluoromethyl-phenyl)-ethyl]-4,5-dihydro-oxazol-2-yl,
4-(1-methyl-2-phenyl-ethyl)-4,5-dihydro-oxazol-2-yl,
4-[2-(2-fluoro-5-trifluoromethyl-phenyl)-ethyl]-4,5-dihydro-oxazol-2-yl,
4-[2-(3-fluoro-5-trifluoromethyl-phenyl)-ethyl]-4,5-dihydro-oxazol-2-yl,
4-[2-(2,5-bis-trifluoromethyl-phenyl)-ethyl]-4,5-dihydro-oxazol-2-yl,
4-[2-(4-chloro-phenyl)-butyl]-4,5-dihydro-oxazol-2-yl,
4-(2-phenyl-butyl)-4,5-dihydro-oxazol-2-yl,
4-[2-(4-trifluoromethyl-phenyl)-propyl]-4,5-dihydro-oxazol-2-yl,
4-[2-(4-trifluoromethyl-phenyl)-butyl]-4,5-dihydro-oxazol-2-yl,
4-[2-(3-trifluoromethyl-phenyl)-propyl]-4,5-dihydro-oxazol-2-yl,
4-[2-(3-trifluoromethyl-phenyl)-butyl]-4,5-dihydro-oxazol-2-yl,
4-[2-(3,5-difluoro-phenyl)-propyl]-4,5-dihydro-oxazol-2-yl,
4-[2-(3,5-difluoro-phenyl)-butyl]-4,5-dihydro-oxazol-2-yl,
4-[2-(4-fluoro-phenyl)-butyl]-4,5-dihydro-oxazol-2-yl,
4-[2-(3,4-difluoro-phenyl)-butyl]-4,5-dihydro-oxazol-2-yl,
4-[2-(2-fluoro-phenyl)-propyl]-4,5-dihydro-oxazol-2-yl,
4-[2-(3,4-dichloro-phenyl)-propyl]-4,5-dihydro-oxazol-2-yl,
4-[2-(3,4-dichloro-phenyl)-butyl]-4,5-dihydro-oxazol-2-yl,
4-[2-(2-fluoro-phenyl)-butyl]-4,5-dihydro-oxazol-2-yl,
4-[2-(2-chloro-phenyl)-ethyl]-4-methyl-4,5-dihydro-oxazol-2-yl,
4-[2-(3-chloro-phenyl)-ethyl]-4,5-dihydro-oxazol-2-yl,
4-[2-(4-chloro-phenyl)-ethyl]-4-methyl-4,5-dihydro-oxazol-2-yl,
4-[2-(3-chloro-phenyl)-ethyl]-4-methyl-4,5-dihydro-oxazol-2-yl,
4-[2-(4-fluoro-phenyl)-ethyl]-4-methyl-4,5-dihydro-oxazol-2-yl,
4-[2-(4-chloro-phenyl)-ethyl]-4,5-dihydro-oxazol-2-yl,
4-[2-(2-chloro-phenyl)-ethyl]-4,5-dihydro-oxazol-2-yl,
4-[2-(3-chloro-phenyl)-butyl]-4,5-dihydro-oxazol-2-yl,
4-(2-phenyl-butyl)-4,5-dihydro-oxazol-2-yl,
4-[2-(2-chloro-6-fluoro-phenyl)-ethyl]-4,5-dihydro-oxazol-2-yl,
4-[2-(2,4-dichloro-phenyl)-ethyl]-4-methyl-4,5-dihydro-oxazol-2-yl,
4-[2-(2-bromo-phenyl)-ethyl]-4,5-dihydro-oxazol-2-yl,
4-[2-(2,5-dichloro-phenyl)-ethyl]-4,5-dihydro-oxazol-2-yl,
4-[2-(3-fluoro-phenyl)-butyl]-4,5-dihydro-oxazol-2-yl,
4-[2-(3-chloro-2-fluoro-phenyl)-butyl]-4,5-dihydro-oxazol-2-yl,
4-[2-(3-chloro-4-fluoro-phenyl)-butyl]-4,5-dihydro-oxazol-2-yl,
4-[2-(3-chloro-5-fluoro-phenyl)-butyl]-4,5-dihydro-oxazol-2-yl,
4-[2-(5-chloro-2-fluoro-phenyl)-butyl]-4,5-dihydro-oxazol-2-yl,
4-(4-fluoro-phenoxymethyl)-4,5-dihydro-oxazol-2-yl,
4-(4-chloro-phenoxymethyl)-4,5-dihydro-oxazol-2-yl,
4-(3,4-dichloro-phenoxymethyl)-4,5-dihydro-oxazol-2-yl,
4-(3,5-dichloro-phenoxymethyl)-4,5-dihydro-oxazol-2-yl,
4-(4-bromo-phenoxymethyl)-4,5-dihydro-oxazol-2-yl,
4-(3-chloro-phenoxymethyl)-4,5-dihydro-oxazol-2-yl,
4-(2,4-difluoro-phenoxymethyl)-4,5-dihydro-oxazol-2-yl,
4-(2-fluoro-phenoxymethyl)-4,5-dihydro-oxazol-2-yl,
4-(3-Phenyl-propyl)-4,5-dihydro-oxazol-2-yl,
4-phenylsulfanylmethyl-4,5-dihydro-oxazol-2-yl,
4-benzenesulfonylmethyl-4,5-dihydro-oxazol-2-yl,
4-benzylsulfanylmethyl-4,5-dihy dro-oxazol-2-yl,
4-(4-chloro-phenylsulfanylmethyl)-4,5-dihydro-oxazol-2-yl,
4-[1-(4-chloro-phenyl)-cyclopropylmethyl]-4,5-dihydro-oxazol-2-yl,
4-[1-(4-chloro-phenyl)-cyclobutylmethyl]-4,5-dihydro-oxazol-2-yl,
4-(1-phenyl-cyclopropylmethyl)-4,5-dihydro-oxazol-2-yl,
4-[(benzyl-ethyl-amino)-methyl]-4,5-dihydro-oxazol-2-yl,
4-[(dimethyl-phenyl-silanyl)-methyl]-4,5-dihydro-oxazol-2-yl,
4-(2,3-dihydro-benzo[1,4]dioxin-6-yl)-4,5-dihydro-oxazol-2-yl,
4-naphthalen-2-yl-4,5-dihydro-oxazol-2-yl,
4-naphthalen-1-yl-4,5-dihydro-oxazol-2-yl,
4-naphthalen-1-ylmethyl-4,5-dihydro-oxazol-2-yl,
4-naphthalen-2-ylmethyl-4,5-dihydro-oxazol-2-yl, 4-(1,2,3,4-tetrahydro-naphthalen-2-yl)-4,5-dihydro-oxazol-2-yl,
4-[2-(3-fluoro-pyridin-4-yl)-ethyl]-4,5-dihydro-oxazol-2-yl,
4-[2-(6-trifluoromethyl-pyridin-2-yl)-ethyl]-4,5-dihydro-oxazol-2-yl,
4-[2-(2-methyl-pyridin-4-yl)-ethyl]-4,5-dihydro-oxazol-2-yl,
4-(2-cyclohexyl-ethyl)-4,5-dihydro-oxazol-2-yl,
4-phenyl-4,5-dihydro-oxazol-2-yl,
4-benzyl-4,5-dihydro-oxazol-2-yl,
4-(2-Benzyl)-4,5-dihydro-oxazol-2-yl,
4-{[(3-Chloro-phenyl)-methyl-amino]-methyl}-4,5-dihydro-oxazol-2-yl,
4-[(Isopropyl-phenyl-amino)-methyl]-4,5-dihydro-oxazol-2-yl,
4-Benzyloxymethyl-4,5-dihydro-oxazol-2-yl,
4-(2-Phenoxy-ethyl)-4,5-dihydro-oxazol-2-yl,
4-(3-Chloro-phenyl)-4,5-dihydro-oxazol-2-yl,
4-(4-Bromo-phenyl)-4,5-dihydro-oxazol-2-yl,
4-(3-Phenoxy-phenyl)-4,5-dihydro-oxazol-2-yl, and
4-(4-Chloro-2-methyl-phenyl)-4,5-dihydro-oxazol-2-yl.

It is within the common knowledge of a synthetic and/or medicinal chemist to construct compounds of the present disclosure by utilizing two oxazoline moieties as above described with the same of different steric configurations.

Hetero-Pseudodimers

In some embodiments, the present disclosure provides hetero-pseudodimers containing two different oxazoline moieties linked by a nitrogen atom, having Formula (I):

I

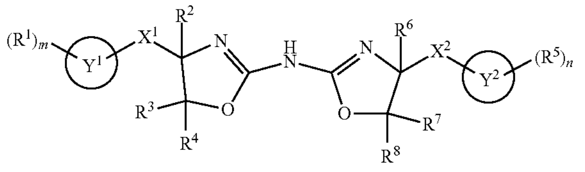

or a pharmaceutically acceptable salt or solvate thereof, wherein each $R^1$ and each $R^5$ are independently:
deuterium,
tritium,
lower alkyl,
lower alkoxy,
lower alkyl substituted by one or more same or different halogens,
lower alkoxy substituted by one or more same or different halogens,
halogen,
phenyl unsubstituted or substituted by one or more same or different halogens,
phenyloxy,
benzyl,
benzyloxy,
COO-lower alkyl,
—O—$(CH_2)_o$—O-lower alkyl,
—NH-cycloalkyl,
cycloalkyl,
piperidin-1-yl, or
tetrahydropyran-4-yloxy;

$X^1$ and $X^2$ are each independently a bond, —$CH(R^{20})$—, —$CH(R^{20})CH(R^{21})$—, —$OCH(R^{20})$—, —$N(R^{20})CH(R^{21})$—, —$CH_2OCH(R^{20})$—, —$CH_2CH_2CH_2$—, —$SCH(R^{20})$—, —$S(O)_2CH(R^{20})$—, —$CH_2SCH_2$—, —$CH_2N(R^{20})CH_2$—, -cycloalkyl-$CH_2$— or —$Si(R^{20})(R^{21})CH_2$—, wherein $R^{20}$ and $R^{21}$ are each independently hydrogen, lower alkyl, lower alkyl substituted by one or more same or different halogens, or benzyl unsubstituted or substituted by one or more same or different substituents selected from the group consisting of alkoxy and halogen;

$R^2$ and $R^6$ are each independently hydrogen, phenyl or lower alkyl;

$R^3$, $R^4$, $R^7$, and $R^8$ are each independently hydrogen, lower alkyl, lower alkoxy, or lower alkyl substituted by one or more same or different halogens, or lower alkoxy substituted by one or more same or different halogens;

$Y^1$ and $Y^2$ are each independently phenyl, naphthyl, thiophenyl, pyridinyl, cycloalkyl, 1,2,3,4-tetrahydro-naphthalen-2-yl, 2,3-dihydrobenzo[1,4]dioxin-6-yl, benzo[1,3]dioxol-5-yl, pyrimidyl, indanyl, 2,3-dihydroindol-1-yl, or 3,4-dihydro-quinolin-1-yl;

m and n are each independently 0, 1, 2 or 3; and o is 1, 2, or 3.

In some embodiments, the hetero-pseudodimer has the Formula (I-A):

I-A

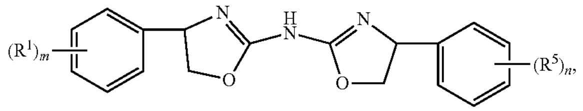

or a pharmaceutically acceptable salt or solvate thereof, wherein $R^1$, $R^5$, m and n are as defined above for Formula (I).

In some embodiments, the compound of Formula (I-A) is a compound of Formula (I-Aa):

I-Aa

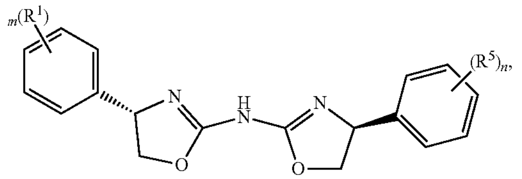

or a pharmaceutically acceptable salt or solvate thereof, wherein $R^1$, $R^5$, m and n are as defined above for Formula (I-A).

In another embodiment, the compound of Formula (I-A) is a compound of Formula (I-Ab):

I-Ab

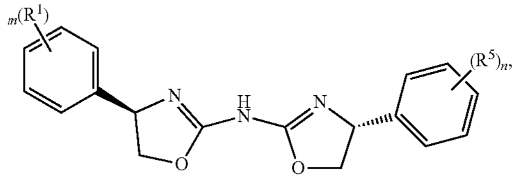

or a pharmaceutically acceptable salt or solvate thereof, wherein $R^1$, $R^5$, m, and n are as defined above for Formula (I-A).

In still another embodiment, the compound of Formula (I-A) is a compound of Formula (I-Ac):

I-Ac

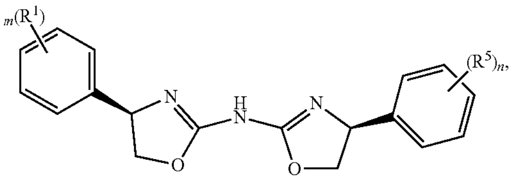

or a pharmaceutically acceptable salt or solvate thereof, wherein $R^1$, $R^5$, m, and n are as defined above for Formula (I-A).

In yet another embodiment, the compound of Formula (I-A) is a compound of Formula (I-Ad):

I-Ad

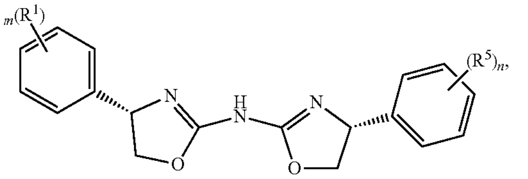

or a pharmaceutically acceptable salt or solvate thereof, wherein $R^1$, $R^5$, m, and n are as defined above for Formula (I-A).

In some embodiments, the compound of the present disclosure is a compound of Formula (I-B):

I-B

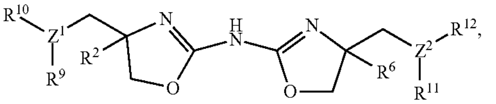

or a pharmaceutically acceptable salt or solvate thereof, wherein $Z^1$ and $Z^2$ are each independently N or CH;

$R^2$ and $R^6$ are each independently hydrogen or lower alkyl;

$R^9$ and $R^{11}$ are each independently hydrogen, lower alkyl, or benzyl unsubstituted or substituted by one or more same or different substituents selected from the group consisting of alkoxy and halogen; and $R^{10}$ and $R^{12}$ are each independently aryl; or $R^9$ and $R^{10}$ together with the N-atom to which they are attached form an 8- to 10-membered heterocyclic group, $R^{11}$ is each independently hydrogen, lower alkyl, or benzyl unsubstituted or substituted by alkoxy or halogen, and $R^{12}$ is aryl; or $R^{11}$ and $R^{12}$ together with the N-atom to which they are attached form an 8- to 10-membered heterocyclic group, $R^9$ is each independently hydrogen, lower alkyl, or benzyl unsubstituted or substituted by alkoxy or halogen, and $R^{10}$ is aryl;

wherein the aryl group is selected from the group consisting of phenyl, naphthyl, 1,2,3,4-tetrahydro-naphthalen-2-yl, and indanyl, and wherein the aryl group is unsubstituted or substituted by one to three substituents, independently selected from the group consisting of cycloalkyl, phenyl, phenyloxy, benzyl, benzyloxy, halogen, lower alkyl, lower alkoxy, piperidin-1-yl, lower alkyl substituted by one or more same or different halogens, and lower alkoxy substituted by one or more same or different halogens.

In some embodiments of the compound of Formula (I-B), $R^9$ and $R^{10}$ together with the N-atom to which they are attached form an 8- to 10-membered heterocyclic group.

In other embodiments, $R^1$ and $R^{12}$ together with the N-atom to which they are attached form an 8- to 10-membered heterocyclic group.

In separate embodiments, $R^9$ and $R^{10}$, together with the N-atom to which they are attached form an 8- to 10-membered heterocyclic group; and $R^{11}$ and $R^{12}$, together with the N-atom to which they are attached form an 8- to 10-membered heterocyclic group.

In one embodiment, the compound of Formula (I-B) is a compound of Formula (I-Ba), I-Ba

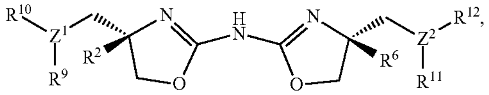

or a pharmaceutically acceptable salt or solvate thereof.

In another embodiment, the compound of Formula (I-B) is a compound of Formula (I-Bb), I-Bb

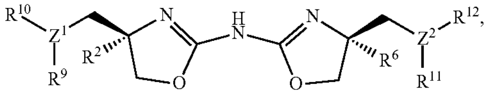

or a pharmaceutically acceptable salt or solvate thereof.

In another embodiment, the compound of Formula (I-B) is a compound of Formula (I-Bc), I-Bc

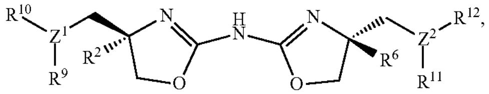

or a pharmaceutically acceptable salt or solvate thereof.

In another embodiment, the compound of Formula (I-B) is a compound of Formula (I-Bd), I-Bd

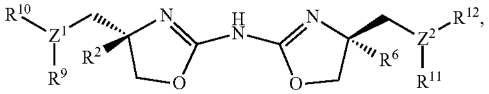

or a pharmaceutically acceptable salt or solvate thereof.

In some embodiments, the hetero-pseudodimer is a compound of Formula (I-C):

I-C

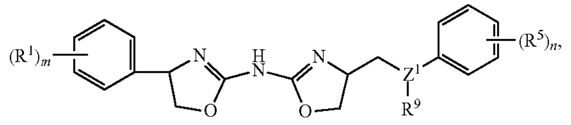

or a pharmaceutically acceptable salt or solvate thereof, wherein $Z^1$ is N or CH;

each $R^1$ and each $R^5$ are independently:

lower alkyl, lower alkoxy, lower alkyl substituted by one or more same or different halogens, lower alkoxy substituted by one or more same or different halogens, halogen, or cycloalkyl;

$R^9$ is hydrogen, lower alkyl, or benzyl unsubstituted or substituted by one or more same or different substituents selected from the group consisting of alkoxy or halogen; and m and n are each independently 0, 1, 2, or 3.

In some embodiments, the compound of Formula (I-C) is a compound of Formula (I-Ca):

I-Ca

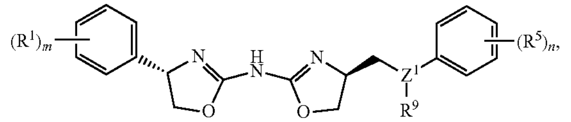

or a pharmaceutically acceptable salt or solvate thereof.

In some embodiments, the compound of Formula (I-C) is a compound of Formula (I-Cb):

I-Cb

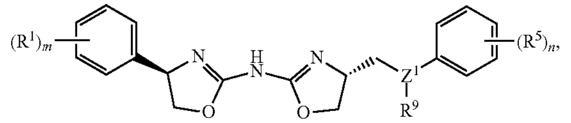

or a pharmaceutically acceptable salt or solvate thereof.

In some embodiments, the compound of Formula (I-C) is a compound of Formula (I-Cc):

I-Cc

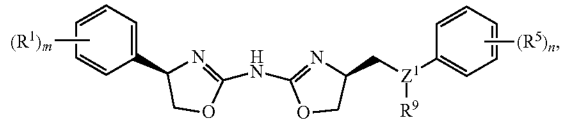

or a pharmaceutically acceptable salt or solvate thereof.

In some embodiments, the compound of Formula (I-C) is a compound of Formula (I-Cd):

I-Cd

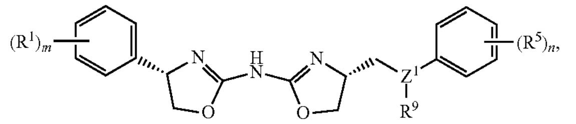

or a pharmaceutically acceptable salt or solvate thereof.

In some embodiments of a compound of Formulae (I-C) through (I-Cd) or a pharmaceutically acceptable salt or solvate thereof, $R^9$ is hydrogen, lower alkyl. In certain embodiments $R^9$ is ethyl.

In separate embodiments of the compound of Formulae (I-C) through (I-Cd) or a pharmaceutically acceptable salt or solvate thereof, $Z^1$ is CH.

In some embodiments, the hetero-pseudodimer is of Formula (I-D):

I-D

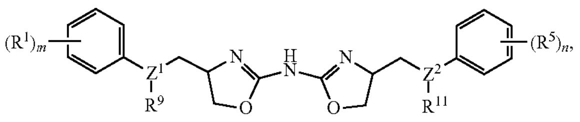

or a pharmaceutically acceptable salt or solvate thereof, wherein $Z^1$ and $Z^2$ are each independently N or CH;

each $R^1$ and each $R^5$ are independently:

lower alkyl, lower alkoxy, lower alkyl substituted by one or more same or different halogens, lower alkoxy substituted by one or more same or different halogens, or halogen;

$R^9$ and $R^{11}$ are each independently hydrogen, lower alkyl or benzyl unsubstituted or substituted by one or more same or different substituents selected from the group consisting of alkoxy or halogen; and m and n are each independently 0, 1, 2, or 3.

In some embodiments, the compound of Formula (I-D) is a compound of Formula (I-Da):

I-Da

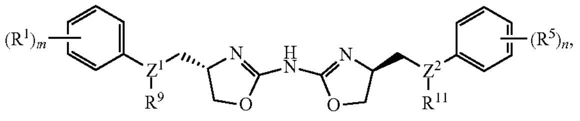

or a pharmaceutically acceptable salt or solvate thereof.

In some embodiments, the compound of Formula (I-D) is a compound of Formula (I-Db):

I-Db

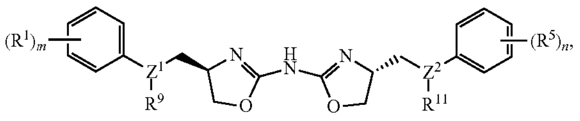

or a pharmaceutically acceptable salt or solvate thereof.

In some embodiments, the compound of Formula (I-D) is a compound of Formula (I-Dc):

I-Dc

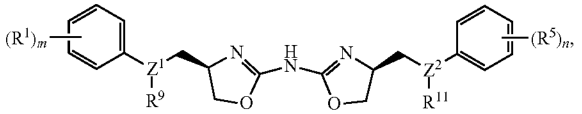

or a pharmaceutically acceptable salt or solvate thereof.

In some embodiments, the compound of Formula (I-D) is a compound of Formula (I-Dd):

I-Dd

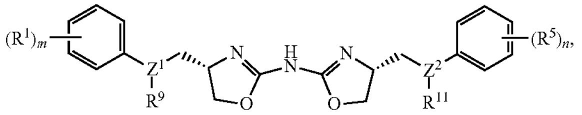

or a pharmaceutically acceptable salt or solvate thereof.

In some embodiments, the compound of the disclosure is a compound of Formulae (I-D) through (I-Dd), wherein m and n are 0, or a pharmaceutically acceptable salt or solvate thereof.

In some embodiments, the compound of the disclosure is a compound of Formulae (I-D) through (I-Dd), wherein each $R^1$ and each $R^5$ are independently same or different halogen or lower alkyl, or a pharmaceutically acceptable salt or solvate thereof.

In some embodiments, the compound of the disclosure is a compound of Formulae (I-D) through (I-Dd), wherein $R^9$ and $R^{11}$ are each independently lower alkyl, or a pharmaceutically acceptable salt or solvate thereof.

In some embodiments, the compound of the disclosure is a compound of Formula (I-D) through (I-Dd), wherein $R^9$ and $R^{11}$ are each independently hydrogen, or a pharmaceutically acceptable salt or solvate thereof.

In certain embodiments, the compounds of the present disclosure include the following compounds:

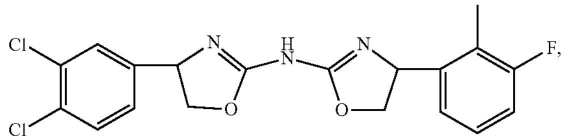

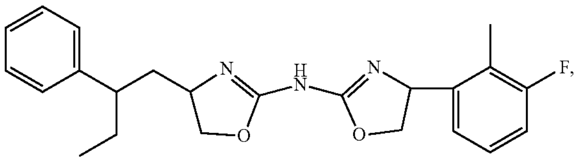

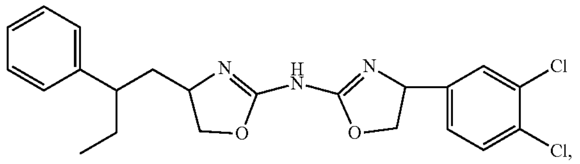

and

-continued

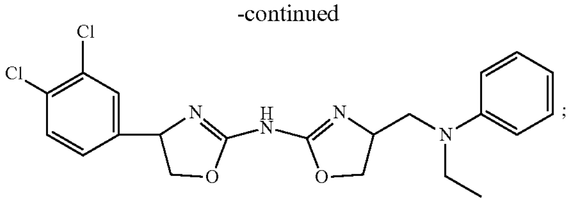

or a pharmaceutically acceptable salt or solvate thereof.

In some embodiments, the compounds of the present disclosure include the following compounds:

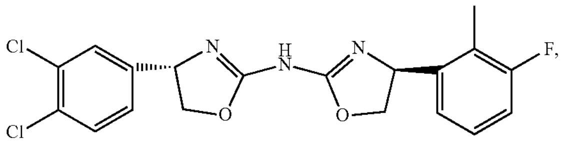

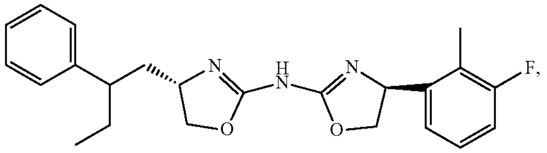

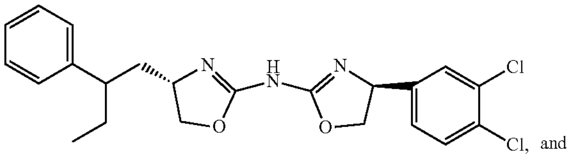

and

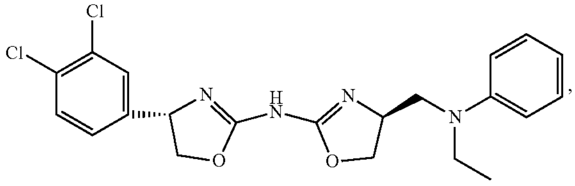

or a pharmaceutically acceptable salt or solvate thereof.

The oxazoline moieties that can be used to construct the compounds of the present disclosure can be any of the oxazoline moieties discussed above for the mono-pseudodimers. It is within the common knowledge of a synthetic and/or medicinal chemist to construct compounds of the present disclosure by utilizing two different oxazoline moieties as above described.

For example, the hetero-pseudodimers of the present disclosure also include the following compounds:

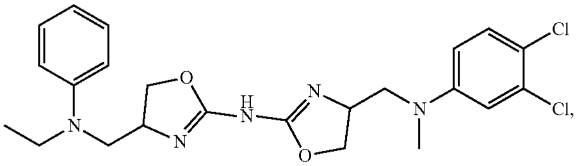

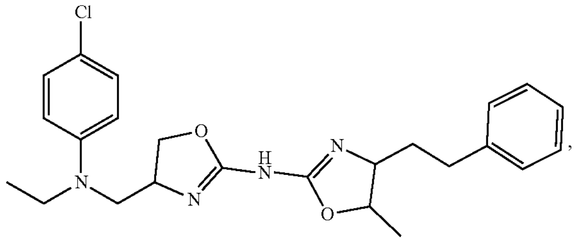

-continued

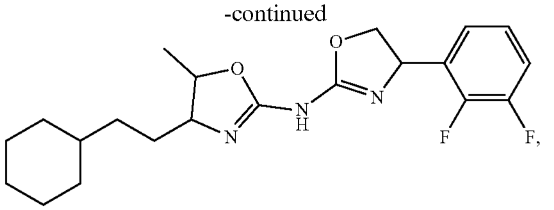

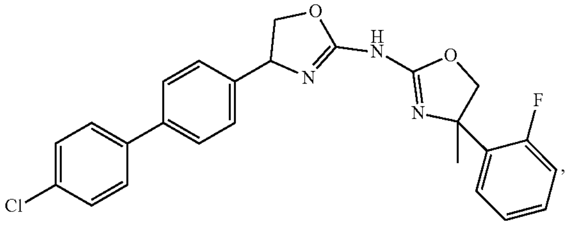

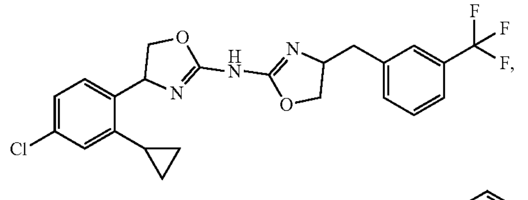

and

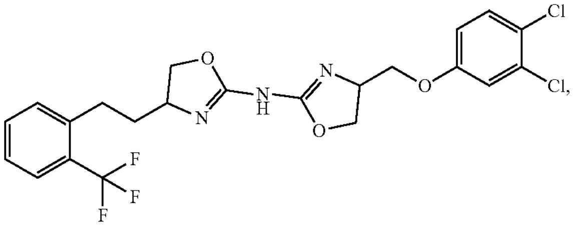

or a pharmaceutically acceptable salt or solvate thereof.

The above embodiments are for the purpose of illustration, the mono-pseudodimers and hetero-pseudodimers of the present disclosure can be constructed by monomers of various structures, and can include oxazoline moieties with various substituents.

In certain embodiments, the pseudodimers or pharmaceutically acceptable salts or solvates thereof described herein are substantially free from corresponding monomers or pharmaceutically acceptable salts or solvates thereof. In some embodiments, the pseudodimers or pharmaceutically acceptable salts or solvates thereof of the invention have a purity of at least 80%, preferably at least 90%, more preferably at least 95%, most preferably at least 97%. In one embodiment, the present disclosure relates to the pseudodimers or pharmaceutically acceptable salts or solvates thereof described herein with a purity of at least 80%, at least 85%, at least 90%, at least 91%, at least 92%, at least 93%, at least 94%, at least 95%, at least 96%, at least 97%. In certain embodiments, the purity is determined through HPLC.

In some embodiments, the present disclosure relates to an enantiomer of a pseudodimer or a pharmaceutically acceptable salt or solvate thereof with an enantiomeric excess (ee) of at least 50%, at least 60%, at least 70%, at least 80%, at least 90%, at least 95%, at least 96%, at least 97%, at least 98%, and at least 99%.

In some embodiments, the present disclosure relates to a diastereomer of a pseudodimer or a pharmaceutically acceptable salt or solvate thereof with a diastereomeric excess (de) of at least 50%, at least 60%, at least 70%, at least 80%, at least 90%, at least 95%, at least 96%, at least 97%, at least 98%, and at least 99%.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

It must be noted that, as used in the specification and the appended claims, the singular forms "a", "an," and "the" include plural forms unless the context clearly dictates otherwise.

Open terms such as "include," "including," "contain," "containing," and the like mean "comprising."

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Certain lower alkyl groups are groups with 1-4 carbon atoms.

As used herein, the term "lower alkoxy" denotes a group wherein the alkyl residue is as defined above and which is attached via an oxygen atom.

As used herein, the term "lower alkyl substituted by one or more same or different halogens" denotes an alkyl group as defined above, wherein at least one hydrogen atom is replaced by halogen, for example $CF_3$, $CHF_2$, $CH_2F$, $CH_2CF_3$, $CH_2CH_2CF_3$, $CH_2CF_2CF_3$ and the like.

As used herein, the term "lower alkoxy substituted by one or more same or different halogens" denotes an alkoxy group as defined above, wherein at least one hydrogen atom is replaced by halogen, for example $OCF_3$, $OCHF_2$, $OCH_2F$, $OCH_2CF_3$, $OCH_2CH_2CF_3$, $OCH_2CF_2CF_3$ and the like.

The term "halogen" denotes chlorine, iodine, fluorine and bromine.

The term "cycloalkyl" is an alkylene ring, containing from 3 to 8, preferably from 3 to 6, carbon ring atoms.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salts" embraces salts with inorganic and organic acids, and inorganic and organic bases. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

The term "treating" or "treatment" refers to administering a therapy in an amount, manner, or mode effective to improve a condition, symptom, or parameter associated with a disorder or to slow or prevent progression of a disorder, to either a statistically significant degree or to a degree detectable to one skilled in the art. An effective amount, manner, or mode can vary depending on the subject and may be tailored to the subject. A subject includes, but not limited to, a human or an animal.

"Therapeutically effective amount" means an amount that is effective to prevent, alleviate or ameliorate symptoms of disease or prolong the survival of the subject being treated.

Synthesis of Compounds

The mono-pseudodimers can be prepared by the method shown in Scheme 1. The desired pseudodimer can be separated from the corresponding monomers. This method is similar to that for preparing aminooxazolines (2) from aminoalcohols (1), as disclosed in U.S. Patent Application Publication Nos. 2009/0105307, 2010/0120864, and 2010/0311798.

Scheme 1

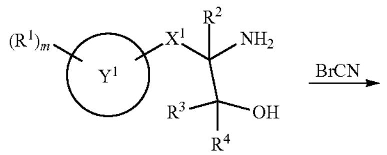

1

-continued

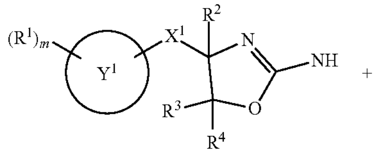

2

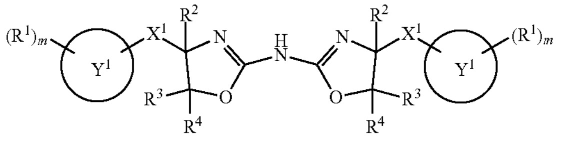

II

Mono-pseudodimers and hetero-pseudodimers can be prepared by the following method as shown in Scheme 2. The aminooxazoline intermediates include, but not limited to those disclosed in U.S. Patent Application Publication Nos. 2009/0105307, 2010/0120864, 2010/0311798, and Galley et al., "Discovery and Characterization of 2-Aminooxazolines as Highly Potent, Selective, and Orally Active TAAR1 Agonists," *ACS Med. Chem. Lett.*, 2016, 7 (2), pp 192-197 ("Galley"). The ethoxyloxazoline intermediates (5) can be prepared from the corresponding aminoalcohols, the same starting material for the aminooxazoline compounds.

Scheme 2
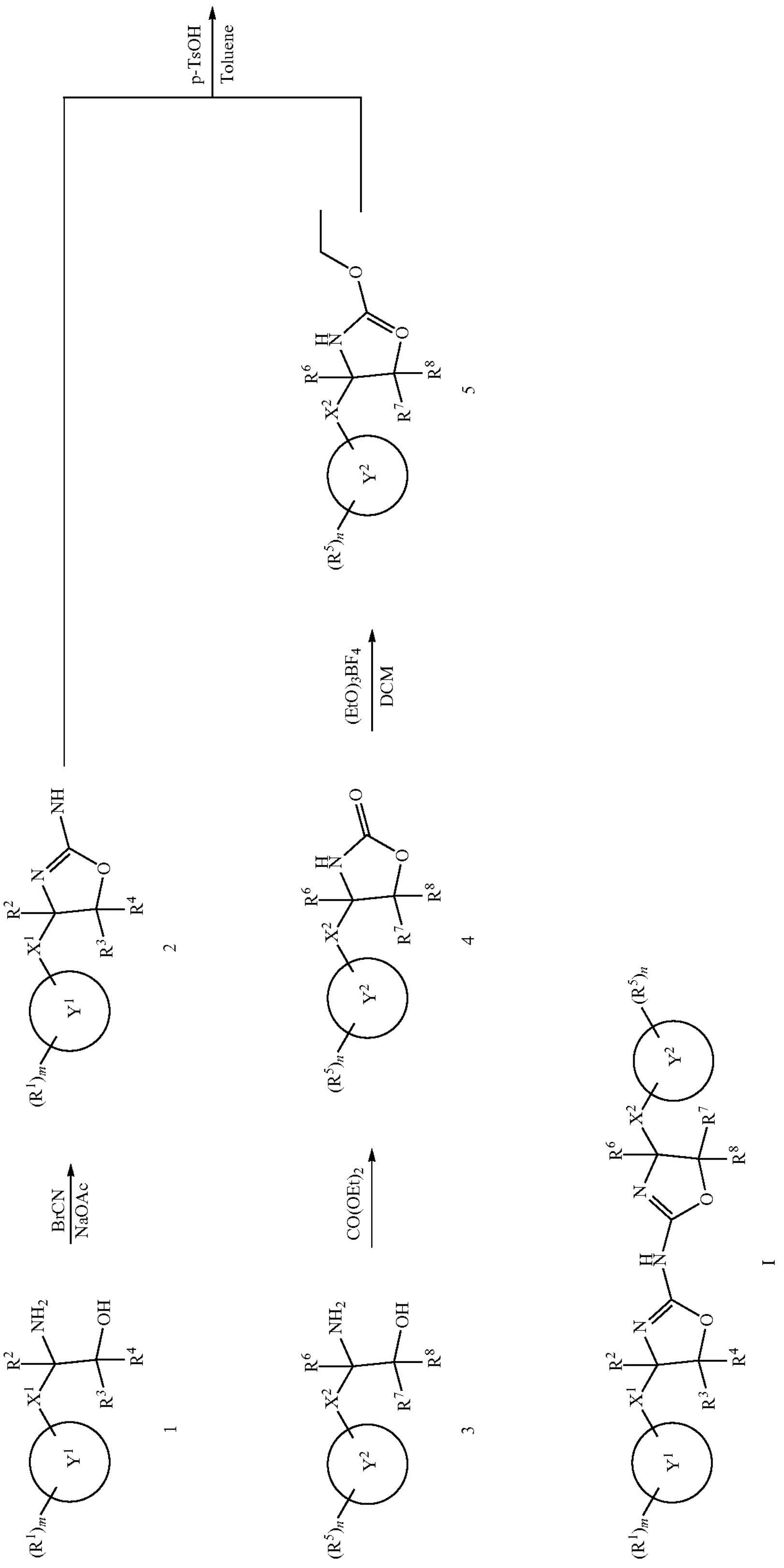
1 2 3 4 5 I

METHOD OF USE

Pain Treatment and Amelioration

In certain embodiments, a pseudodimer or a pharmaceutically acceptable salt or solvate thereof of the present disclosure (alternatively, as a compound of the present disclosure) is used in combination with at least one other therapeutic agent. The other therapeutic agent can be, but is not limited to, a μ-opioid agonist, a non-opioid analgesic, a non-steroidal anti-inflammatory agent, a Cox-II inhibitor, an anti-emetic, a β-adrenergic blocker, an anticonvulsant, an antidepressant, a $Ca^{2+}$-channel blocker, an anticancer agent, or a mixture thereof.

A compound of the present disclosure can be used to treat acute, chronic pain (which includes but is not limited to, neuropathic pain, postoperative pain, and inflammatory pain), or surgical pain. Examples of pain that can be treated using a compound of the present disclosure include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

Acute pain includes, but is not limited to, perioperative pain, postoperative pain, post-traumatic pain, acute disease related pain, and pain related to diagnostic procedures, orthopedic manipulations, and myocardial infarction. Acute pain in the perioperative setting includes pain because of pre-existing disease, the surgical procedure, e.g., associated drains, chest or nasogastric tubes, or complications, or a combination of disease-related and procedure-related sources.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

A compound of the present disclosure can be used to treat pain associated with inflammation or with an inflammatory disease in a patient. Such pain can arise where there is an inflammation of the body tissue which can be a local inflammatory response or a systemic inflammation. For example, a compound of the present disclosure can be used to treat pain associated with inflammatory diseases including, but not limited to, organ transplant rejection; reoxygenation injury resulting from organ transplantation (see Grupp et al., *J. Mol, Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including comeal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microaluminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. A compound of the present disclosure can also be used to treat pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

A compound of the present disclosure can be used to treat pain associated with nerve injury (i.e., neuropathic pain). Chronic neuropathic pain is a heterogenous disease state with an unclear etiology. In chronic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Chronic neuropathic pain can be caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiences. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

A compound of the present disclosure can be used to treat pain associated with migraine including, but not limited to, migraine without aura ("common migraine"), migraine with aura ("classic migraine"), migraine without headache, basilar migraine, familial hemiplegic migraine, migrainous infarction, and migraine with prolonged aura.

A compound of the present disclosure can also be used as an agent to treat withdrawal from alcohol addiction or drug addiction; as an agent to treat addictive disorders; as an agent to treat a pruritic condition; and in treating or ameliorating constipation and diarrhea.

Due to their activity, the compounds of the present disclosure are advantageously useful in human and veterinary medicine. As described above, the compounds of the present disclosure are useful for treating pain in a patient in need thereof. The compounds of the present disclosure can be administered to any patient requiring modulation of the opioid receptors. The term "patient" as used herein refers to any animal that may experience the beneficial effects of a compound of the present disclosure. Foremost such animals are mammals, e.g., humans and companion animals, although the invention is not intended to be so limited.

TAAR1 Modulation

In some embodiments, the present disclosure provides a method of activating TAAR1 comprising administering to a subject in need thereof an effective amount of a compound disclosed herein.

TAAR1 is a 7-transmembrane domain G-protein coupled receptor (Gas) that responds to various trace amines ("TAs") (Lindemann et al., "Trace amine-associated receptors form structurally and functionally distinct subfamilies of novel G protein-coupled receptors," *Genomics* 85 (3): 372-85 (2005)). TAs include β-phenylethylamine, p-tyramine, tryptamine, octopamine, and synephrine. TAs are activated by thyroid hormone derivative, COMT (Catechol-O-Methyltransferase) products, and amphetamine. TAAR1 has low affinity for classic monoamines. TAAR1 signals through the cAMP/PKA (Protein Kinase A)/CREB (cAMP Responsive Element Binding Protein) and the PKC (Protein Kinase C)/$Ca^{++}$/NFAT (Nuclear Factor of Activated T-cells) pathways.

TAAR1 is expressed in brain, spinal cord, and peripheral tissues in rodents and monkeys (see Xie et al., "Trace Amine-Associated Receptor 1 as a Monoaminergic Modulator in Brain," *Biochem. Pharmacol.* 78(9): 1095-1104 (2009)). It has been reported that human TAAR1 mRNA was detected by quantitative reverse transcription (RT)-PCR in low levels in discrete regions within the central nervous system (CNS) and in several peripheral tissues. Moderate levels were expressed in stomach, low levels expressed in amygdala, kidney, lung, and small intestine, whereas trace amounts were expressed in cerebellum, dorsal root ganglia, hippocampus, hypothalamus, liver, medulla, pancreas, pituitary, pontine reticular formation, prostate, skeletal muscle, and spleen (see Borowsky et al., "Trace amines: Identification of a family of mammalian G protein-coupled receptors," *Proc. Natl. Acad. Sci. U.S.A* 98(16): 8966-8971 (2001)).

In vitro, TAAR1 activation drives the PKA and PKC cellular signaling cascades that result in inhibition of monoamine uptake and transporter reversal (efflux) in DAT (Dopamine Transporter)/TAAR1, NET (Norepinephrine Transporter)/TAAR1, and SERT (Serotonin Transporter)/TAAR1 co-transfected cells, as well as in mouse and primate striatal (DAT, SERT) and thalamic (NET) synaptosomes ex vivo.

In vivo, TAAR1 selective activation prevents both hyperdopaminergic- and hypoglutamatergic-induced hyperlocomotion in rodents, suggesting anxiolytic- and antipsychotic-like effects (see Revel et al., "TAAR1 activation modulates monoaminergic neurotransmission, preventing hyperdopaminergic and hypoglutamatergic activity," *Proc. Natl. Acad. Sci. U.S.A* 108(20): 8485-8490 (2011)).

Additionally, TAAR1 has been implicated as playing a role in schizophrenia, depression, addiction and Parkinson's disease.

Pharmaceutical Compositions and Administration

When administered to a patient, a compound of the present disclosure can be administered as a component of a composition that comprises a pharmaceutically acceptable carrier or excipient. A compound of the present disclosure can be administered by any appropriate route, as determined by the medical practitioner. Methods of administration may include intradermal, intramuscular, intraperitoneal, parenteral, intravenous, subcutaneous, intranasal, epidural, oral, sublingual, buccal, intracerebral, intravaginal, transdermal, transmucosal, rectal, by inhalation, or topical (particularly to the ears, nose, eyes, or skin). Delivery can be either local or systemic. In certain embodiments, administration will result in the release of a compound of the present disclosure into the bloodstream.

Pharmaceutical compositions of the application can take the form of solutions, suspensions, emulsions, tablets, pills, pellets, powders, multi-particulates, capsules, capsules containing liquids, capsules containing powders, capsules containing multi-particulates, lozenges, sustained-release formulations, suppositories, transdermal patches, transmucosal films, sub-lingual tablets or tabs, aerosols, sprays, or any other form suitable for use. In one embodiment, the composition is in the form of a tablet. In another embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

Pharmaceutical compositions of the application preferably comprise a suitable amount of a pharmaceutically acceptable excipient so as to provide the form for proper administration to the patient. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to a patient. Water is a particularly useful excipient when a compound of the present disclosure is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

In certain embodiments, the compounds of the present disclosure are formulated for oral administration. A compound of the present disclosure to be orally delivered can be in the form of tablets, capsules, gelcaps, caplets, lozenges, aqueous or oily solutions, suspensions, granules, powders, emulsions, syrups, or elixirs, for example. When a compound of the present disclosure is incorporated into oral tablets, such tablets can be compressed, tablet triturates, enteric-coated, sugar-coated, film-coated, multiply compressed or multiply layered.

An orally administered compound of the present disclosure can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., $16^{th}$ ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in *Pharmaceutical Dosage Forms: Disperse Systems*, (Lieberman, Rieger and Banker, eds.) published by Marcel Dekker, Inc.

When a compound of the present disclosure is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a compound of the present disclosure is to be injected parenterally, it can be, e.g., in the form of an isotonic sterile solution. A compound of the present disclosure can also be in the form of a powder for reconstitution as an injectable formulation.

In certain embodiments, a compound of the present disclosure is formulated into a pharmaceutical composition for intravenous administration. Typically, such compositions comprise sterile isotonic aqueous buffer. Where necessary, the compositions can also include a solubilizing agent. A compound of the present disclosure for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a compound of the present disclosure is to be administered by infusion, it can be dispensed, for example, with an infusion bottle containing sterile pharmaceutical grade water or saline. Where a compound of the present disclosure is administered by injection, an ampule of sterile water for injection or saline can be provided so that the ingredients can be mixed prior to administration.

When a compound of the present disclosure is to be administered by inhalation, it can be formulated into a dry aerosol, or an aqueous or partially aqueous solution.

In another embodiment, a compound of the present disclosure can be delivered in a vesicle, in particular a liposome (see Langer, *Science* 249:1527-1533 (1990); and Treat et al., *Liposomes in the Therapy ofInfectious Disease and Cancer* 317-327 and 353-365 (1989)).

In certain embodiments, a compound of the present disclosure is administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as, sialastic membranes, or fibers.

In certain embodiments, a compound of the present disclosure can be delivered in an immediate release form. In other embodiments, a compound of the present disclosure can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a compound of the present disclosure to treat or prevent the Condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the compound of the present disclosure and can thus reduce the occurrence of adverse side effects.

Controlled- or sustained-release compositions can initially immediately release an amount of a compound of the present disclosure that promptly produces the desired therapeutic or prophylactic effect, and gradually and continually release other amounts of the compound of the present disclosure to maintain a level of therapeutic or prophylactic effect over an extended period of time. To maintain a constant level of the compound of the present disclosure in the body, the compound of the present disclosure can be released from the dosage form at a rate that will replace the amount of compound of the present disclosure being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release means for use according to the present disclosure may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, “Dental Applications” (pp. 115-138) in *Medical Applications of Controlled Release, Vol. 2, Applications and Evaluation*, R. S. Langer and D. L. Wise eds., CRC Press (1984). Other controlled- or sustained-release systems that are discussed in the review by Langer, *Science* 249:1527-1533 (1990) can be selected for use according to the present disclosure. In one embodiment, a pump can be used (Langer, *Science* 249:1527-1533 (1990); Sefton, *CRC Crit. Ref Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg* 71:105 (1989)). In yet another embodiment, a controlled- or sustained-release system can be placed in proximity of a target of a compound of the present disclosure, e.g, the spinal column, brain, or gastrointestinal tract, thus requiring only a fraction of the systemic dose.

When in tablet or pill form, a pharmaceutical composition of the invention can be coated to delay disintegration and absorption in the gastrointestinal tract, thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions of the invention include single unit dosage forms suitable for oral administration such as, but not limited to, tablets, capsules, gelcaps, and caplets that are adapted for controlled- or sustained-release.

The amount of the compound of the present disclosure that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the extent of the Condition to be treated, and can be decided according to the judgment of a practitioner and/or each patient’s circumstances. Variations in dosing may occur depending upon typical factors such as the weight, age, gender and physical condition (e.g., hepatic and renal function) of the patient being treated, the affliction to be treated, the severity of the symptoms, the frequency of the dosage interval, the presence of any deleterious side-effects, and the particular compound utilized, among other things.

Pain Biological Assays

In Vivo Assays for Pain

Test Animals:

Each experiment uses rats weighing between 200-260 g at the start of the experiment. The rats are group-housed and have free access to food and water at all times, except prior to oral administration of a compound of the present disclosure when food is removed for about 16 hours before dosing. A control group acts as a comparison to rats treated with a compound of the present disclosure. The control group is administered the carrier for the compound of the present disclosure. The volume of carrier administered to the control group is the same as the volume of carrier and compound of the present disclosure administered to the test group.

Acute Pain:

To assess the actions of a compound of the present disclosure for the treatment or prevention of acute pain, the rat tail flick can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a compound of the present disclosure. Data are expressed as tail flick latency(s) and the percentage of the maximal possible effect (% MPE), i.e., 20 seconds, is calculated as follows:

$$\%\ MPE = \frac{[(\text{post administration latency}) - (\text{pre-administration latency})]}{(20\ s - \text{pre-administration latency})} \times 100$$

The rat tail flick test is described in F. E. D’Amour et al., “A Method for Determining Loss of Pain Sensation,” *J. Pharmacol. Exp. Ther.* 72:74-79 (1941).

To assess the actions of a compound of the present disclosure for the treatment or prevention of acute pain, the rat hot plate test can also be used. Rats are tested using a hot plate apparatus consisting of a clear plexiglass cylinder with a heated metal floor maintained at a temperature of 48-52° C. (Model 7280, commercially available from Ugo Basile of Italy). A rats is placed into the cylinder on the hot plate apparatus for a maximum duration of 30 s, or until it exhibits a nocifensive behavior (behavioral endpoint), at which time it is removed from the hot plate, and the response latency recorded. Hot plate latencies are measured immediately before (pre-treatment) and 1, 3, and 5 hours following administration of a compound of the present disclosure. The nocifensive behavioral endpoint is defined as any of the following: 1) paw withdrawal, either as a sustained lift or with shaking or licking; 2) alternating foot lifting; 3) excape or attempted escape from the testing device; or 4) vocalization. Data are expressed as response latency(s) and the percentage of the maximal possible effect is calculated as described above for the tail flick test. The hot plate test is described in G. Woolfe and A. D. MacDonald, *J. Pharmacol. Exp. Ther.* 80:300-307 (1944).

Inflammatory Pain:

To assess the actions of a compound of the present disclosure for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 μL intraplantar injection of 50% FCA. Prior to injection of FCA (baseline) and 24 hour post injection, the animal is assessed for response to noxious mechanical stimuli by determining the PWT, as described below. Rats are then administered a single injection of 1, 3, or 10 mg/kg of either a compound of the present disclosure; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

$$\%\ \text{Reversal} = \frac{[(\text{post administration } PWT) - (\text{pre-administration } PWT)]}{[(\text{baseline } PWT) - (\text{pre-administration } PWT)]} \times 100$$

Neuropathic Pain:

To assess the actions of a compound of the present disclosure for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\%\ \text{Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation ("SNL") model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a compound of the present disclosure. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia:

The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The rat is gently restrained, its hindpaw is placed on a small round platform, and punctate pressure is applied to the dorsal surface of the hindpaw in a graded manner. The maximum weight that is applied to the hind paw is set at 250 g and the end point is taken as complete withdrawal of the paw. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia:

The plantar test can be used to assess thermal hyperalgesia. For this test, hind paw withdrawal latencies to a noxious thermal stimulus applied to the plantar surface of the hindpaw are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia:

To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Assessment of Respiratory Depression:

To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., *Intensive Care Med.* (26): 585-591 (2000).

Assessment of Gastric Motility:

Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

EXAMPLES

Example 1

Preparation of (4S)-4-(3,4-dichlorophenyl)-N-[(4S)-4-(3,4-dichlorophenyl)-4,5-dihydro-1,3-oxazol-2-yl]-4,5-dihydro-1,3-oxazol-2-amine (8)

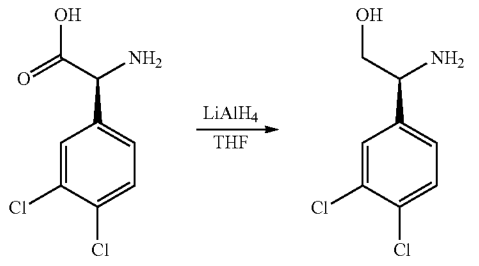

6

To a 250 ml flame dry round bottom flask was added $LiAlH_4$ (2.28 g, 60 mmol, 2 eq.) and 70 ml THF. The solution was cooled to 0° C. and (2S)-2-amino-2-(3,4-dichlorophenyl)acetic acid (6.58 g, 29.9 mmol, 1 eq.) was added portion wise. After the addition was complete, the reaction mixture was heated to reflux under $N_2$ for 16 h. The resulting mixture was then cooled to 0° C. and quenched slowly with 5% $NaHCO_3$ (10 ml). All volatiles were removed and the residue was triturated and suspended in EtOAc (100 ml). After 2 h, the white precipitate was filtered and the filtrate concentrated to give (2S)-2-amino-2-(3,4-dichlorophenyl)ethan-1-ol (6) (5.1 g, 83%).

$^1$HNMR ($D_2O$) δ: 7.54 (d, 1H), 7.52 (s, 1H), 7.25 (d, 1H), 4.39 (t, 1H), 3.89 (dd, 1H), 3.81 (dd, 1H) ppm; MS: (m/e): 207 (M+1)

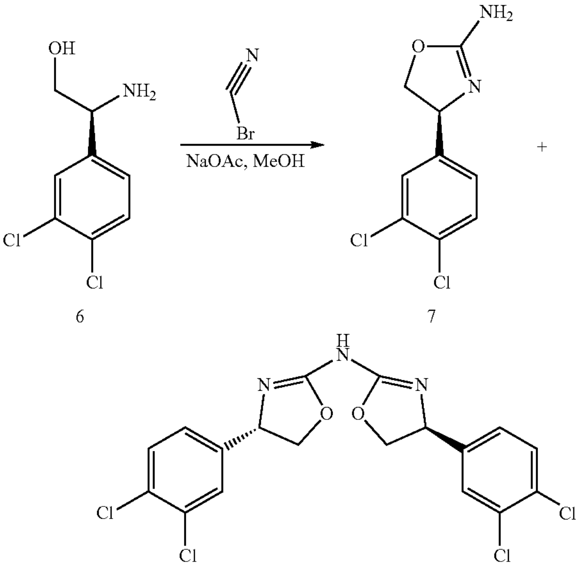

6 7 8

To a stirred suspension of (2S)-2-amino-2-(3,4-dichlorophenyl)ethan-1-ol (1 g, 4.85 mmol, 1 eq.) and sodium acetate (0.796 g, 9.7 mmol, 2 eq.) in anhydrous methanol (40 ml) was added dropwise a solution of cyanogen bromide (0.616 g, 5.82 mmol, 1.2 eq.) in methanol (10 ml). The resulting yellow solution was then stirred at room temperature for 16 h. LCMS indicated completion. The mixture was treated with saturated aq, $NaHCO_3$ (10 ml) dropwise and stirring was continued for 2 h. Most of the methanol was removed under reduced pressure without any heating and crude product extracted with EtOAc (3×50 ml). The combined organic phase was dried over $Na_2SO_4$ and concentrated in vacuo. The crude product was purified by column chromatography (Biotage KP-NH® Flash-$NH_2$; gradient: Hexane/EtOAc (0% to 100% over 40 minutes) to give (S)-4-(3,4-dichlorophenyl)-4,5-dihydro-1,3-oxazol-2-amine (0.62 g, 55%) (7) as a major white solid product, and a minor product (4S)-4-(3,4-dichlorophenyi)-N-[(4S)-4-(3,4-dichlorophenyl)-4,5-dihydro-1,3-oxazol-2-yl]-4,5-dihydro-1,3-oxazol-2-amine (8) (83 mg, 4%). Compound (8) upon separation has a purity of about 97% determined by HPLC.

(S)-4-(3,4-dichlorophenyl)-4,5-dihydro-1,3-oxazol-2-amine (7)

$^1$HNMR ($CDCl_3$) δ: 7.38 (d, 1H), 7.26 (s, 1H), 7.11 (d, 1H), 5.05 (t, 1H), 4.63 (t, 1H), 3.4 (br, 2H) ppm; MS: (m/e): 232 (M+1)

(4S)-4-(3,4-dichlorophenyl)-N-[(4S)-4-(3,4-dichlorophenyl)-4,5-dihydro-1,3-oxazol-2-yl]-4,5-dihydro-1,3-oxazol-2-amine (8)

$^1$HNMR ($CDCl_3$) δ: 7.46-7.37 (m, 2H), 7.30-7.24 (m, 2H), 7.15-7.12 (m, 2H), 5.12 (b, 1H), 4.74-4.71 (m, 2H), 4.78-4.51 (m, 1H), 4.16 (b, 1H), 3.99-3.96 (m, 1H) ppm; MS: (m/e): 446 (M+1)

Example 2

The Effect of the Pseudodimer Compound (8) on Spinal Nerve Ligation-Induced ("SNL") Mechanical Hyperalgesia in Rats Mechanical Hyperalgesia:

Representative compounds of the present disclosure are tested in the spinal nerve ligation ("SNL") induced mechanical hyperalgesia model in male, Sprague-Dawley rats. Sensitivity to noxious mechanical stimuli was measured in animals using the paw pressure test to assess mechanical hyperalgesia. In rats, hind paw withdrawal thresholds ("PWT"), measured in grams, in response to a noxious mechanical stimulus were determined using an analgesymeter (Model 7200, commercially available from Ugo Basile of Italy), as described in Stein (*Biochemistry & Behavior* 31: 451-455 (1988)). The rat's paw was placed on a small platform, and weight was applied in a graded manner up to a maximum of 250 grams. The endpoint was taken as the weight at which the paw was completely withdrawn. PWT was determined once for each rat at each time point. PWT can be measured only in the injured paw, or in both the injured and non-injured paw. Rats were tested prior to surgery to determine a baseline, or normal, PWT. Rats were tested again 4 weeks post-surgery and at different times after (e.g., 1, 3, and 5 hr) drug administration. Gabapentin was implemented as the positive control. A SNL control was implemented to determine the PWT of a rat having no drug administration. A sham control was implemented to determine the PWT of a rat having neither surgery nor drug administration. An increase in PWT following drug administration indicates that the test compound reduces mechanical hyperalgesia.

Rats are transferred to an elevated testing cage with a wire mesh floor and allowed to acclimate for five to ten minutes. A slightly blunted needle is touched to the plantar surface of the hindpaw causing a dimpling of the skin without penetrating the skin. Administration of the needle to control paws typically produces a quick flinching reaction too short to be timed with a stopwatch, and arbitrarily given a withdrawal time of 0.5 second. The operated side paw of neuropathic animals exhibits an exaggerated withdrawal response to the blunted needle. A maximum withdrawal time of ten seconds is used as a cutoff time. Withdrawal times for both paws of the animals are measured three times at each time point with a five-minute recovery period between applications. The three measurements are used to generate an average withdrawal time for each time point.

Compound (8) reduced SNL-induced mechanical hyperalgesia in rats when dosed orally at 5 mg/kg one hour before testing. Compound (8) showed robust efficacy in the SNL-induced mechanical hyperalgesia model of neuropathic pain in rats, with 85% max reversal (See FIG. 1). In the experiment, male, Sprague-Dawley rats, 289-359 g (n=6-9/group) were baselined for left hind paw threshold before (Pre-Sx) and then 4 weeks post-SNL surgery. Compound (8) and gabapentin the positive control, were administered 1 hour prior to testing. Compound (8) was formulated in 25% HPBCD and gabapentin was dissolved in 0.9% NS. Data were analyzed by a two-way ANOVA followed by a Bonferroni multiple comparisons test.

Example 3

Synthesis of Oxazolidinones

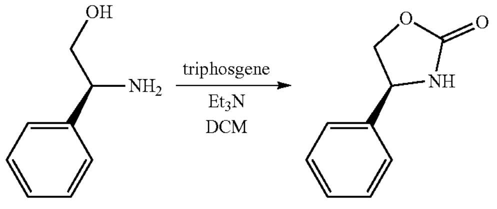

9

10

General procedure for the synthesis of oxazolidinone: (4S)-4-phenyl-1,3-oxazolidin-2-one (10). To (2S)-2-amino-2-phenylethan-1-ol hydrochloride (9) (1.00 g, 7.30 mmol, 1 equiv) in DCM (35 mL) was added $Et_3N$ (2.55 mL, 18.3 mmol, 2.5 equiv). The mixture was cooled to 0° C., and a solution of triphosgene (2.37 g, 8.00 mmol, 1.1 equiv) in DCM (35 mL) was added dropwise. The mixture was allowed to warm slowly to rt and stirred for 16 h. The mixture was cooled to 0° C. before it was diluted with EtOAc (100 mL) and $H_2O$ (100 mL). The mixture was allowed to stir at rt until layers became clear. The layers were separated, and the aqueous layer was extracted with EtOAc (2×50 mL). The combined organic layers were washed with water, brine, dried over $MgSO_4$, filtered, and concentrated. The resultant residue was purified by column chromatography (24 g ISCO EtOAc/hexanes 0 to 100%) to afford (4S)-4-phenyl-1,3-oxazolidin-2-one (10) (0.819 g, 69%): $^1$HNMR ($CDCl_3$) δ: 7.42-7.34 (m, 5H), 5.56 (broad s, 1H), 4.97 (t, 1H), 4.75 (t, 1H), 4.21 (dd, 1H) ppm; MS: (m/e): 164 (M+1).

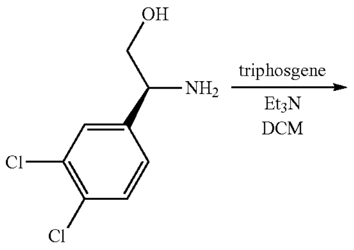

11

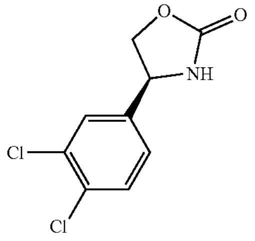

12

(4S)-4-(3,4-dichlorophenyl)-1,3-oxazolidin-2-one (12)

The general procedure for oxazolidinone synthesis was used starting with (2S)-2-amino-2-(3,4-dichlorophenyl)ethan-1-ol hydrochloride (11) (1.00 g, 4.10 mmol) to afford (4S)-4-(3,4-dichlorophenyl)-1,3-oxazolidin-2-one (12) (0.995 g, quantitative): $^1$HNMR ($CDCl_3$) δ: 7.50 (d, 1H), 7.45 (d, 1H), 7.19 (dd, 1H), 6.24 (broad s, 1H), 4.94 (t, 1H), 4.75 (t, 1H), 4.15 (dd, 1H) ppm; MS: (m/e): 232, 234 (M+1).

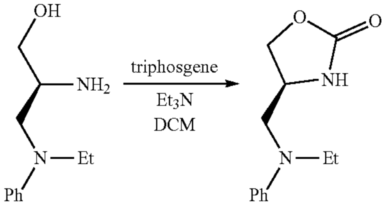

13 14

(4S)-4-{[ethyl(phenyl)amino]methyl}-1,3-oxazolidin-2-one (14)

The general procedure for oxazolidinone synthesis was used starting with (2S)-2-amino-3-[ethyl(phenyl)amino]propan-1-ol (13) (0.620 g, 3.20 mmol) (prepared as described in WO2008/098857) to afford (4S)-4-{[ethyl(phenyl)amino] methyl}-1,3-oxazolidin-2-one (14) (0.473 g, 69%): MS: (m/e): 221 (M+1).

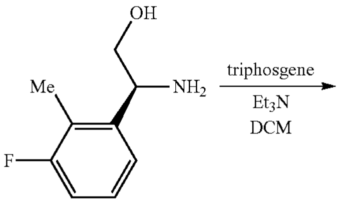

15

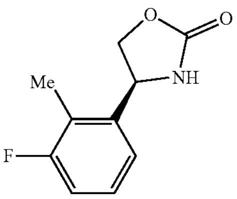

16

(4s)-4-(3-fluoro-2-methylphenyl)-1,3-oxazolidin-2-one (16)

the general procedure for oxazolidinone synthesis was used starting with (2S)-2-amino-2-(3-fluoro-2-methylphenyl)ethan-1-ol hydrochloride (15) (0.300 g, 1.46 mmol) to afford (4S)-4-(3-fluoro-2-methylphenyl)-1,3-oxazolidin-2-one (16) (0.268 g, 94%): MS: (m/e): 196 (M+1).

Example 4

Synthesis of Oxazoline Ethers

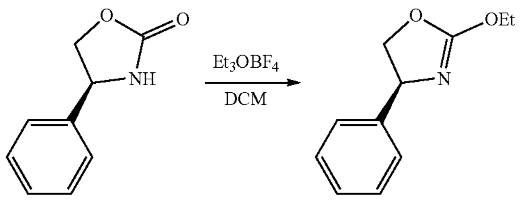

10 17

General procedure for the synthesis of oxazoline ethers: (4S)-2-ethoxy-4-phenyl-4,5-dihydro-1,3-oxazole (17). To (4S)-4-phenyl-1,3-oxazolidin-2-one (10) (0.405 g, 2.48 mmol, 1 equiv) in DCM (3.00 mL) cooled to 0° C. was added a solution of triethyloxonium tetrafluoroborate (1.41 g, 7.44 mmol, 3 equiv) in DCM (3.00 mL). The mixture was allowed to warm slowly to rt and stirred for 18 h. The mixture was diluted with EtOAc (20 mL) and poured slowly over a cooled (0° C.) solution of saturated aqueous $NaHCO_3$ (25 mL). The layers were separated, and the aqueous layer was extracted with EtOAc (2×20 mL). The combined organic layers were washed with brine, dried over $Na_2SO_4$, filtered, and concentrated to afford (4S)-2-ethoxy-4-phenyl-4,5-dihydro-1,3-oxazole (17) (0.428 g, 90%): $^1$HNMR ($CDCl_3$) δ: 7.38-7.28 (m, 5H), 5.15 (dd, 1H), 4.47 (dd, 1H), 4.42-4.35 (m, 2H), 4.20 (t, 1H), 1.41 (t, 3H) ppm; MS: (m/e): 192 (M+1).

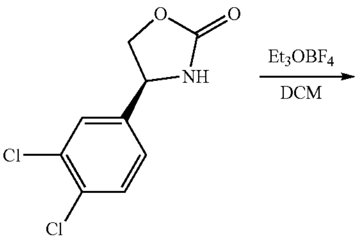

12

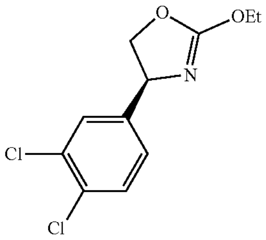

18

(4S)-4-(3,4-dichlorophenyl)-2-ethoxy-4,5-dihydro-1,3-oxazole (18)

The general procedure for oxazoline ether synthesis was used starting with (4S)-4-(3,4-dichlorophenyl)-1,3-oxazolidin-2-one (12) (0.274 g, 1.18 mmol) to afford (4S)-4-(3,4-dichlorophenyl)-2-ethoxy-4,5-dihydro-1,3-oxazole (18) (0.280 g, 91%): $^1$HNMR ($CDCl_3$) δ: 7.43 (d, 1H), 7.40 (d, 1H), 7.13 (dd, 1H), 5.12 (dd, 1H), 4.74 (t, 1H), 4.42-4.35 (m, 2H), 4.12 (t, 1H), 1.41 (t, 3H) ppm; MS: (m/e): 278, 280 (M+1).

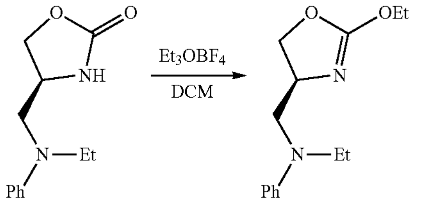

14 19

N-{[(4S)-2-ethoxy-4,5-dihydro-1,3-oxazol-4-yl]methyl}-N-ethylaniline (19)

The general procedure for oxazoline ether synthesis was used starting with (4S)-4-{[ethyl(phenyl)amino]methyl}-1,3-oxazolidin-2-one (14) (0.275 g, 1.25 mmol) to afford N-{[(4S)-2-ethoxy-4,5-dihydro-1,3-oxazol-4-yl]methyl}-N-ethylaniline (19) (0.320 g, quantitative): $^1$HNMR ($CDCl_3$) δ: 7.23 (dd, 2H), 6.77 (d, 2H), 6.71 (dd, 1H), 4.45-4.35 (m, 1H), 4.28 (q, 2H), 4.20 (dd, 1H), 3.57-3.48 (m, 2H), 3.43-3.36 (m, 2H), 3.25 (dd, 1H), 1.37 (t, 3H), 1.13 (t, 3H) ppm; MS: (m/e): 249 (M+1).

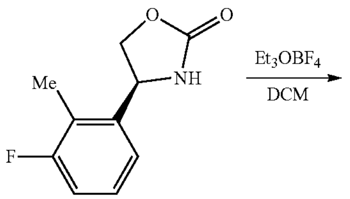

16

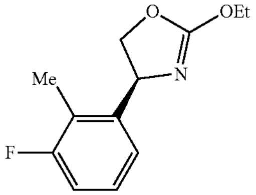

20

(4S)-2-ethoxy-4-(3-fluoro-2-methylphenyl)-4,5-dihydro-1,3-oxazole (20)

The general procedure for oxazoline ether synthesis was used starting with (4S)-4-(3-fluoro-2-methylphenyl)-1,3-oxazolidin-2-one (16) (0.050 g, 0.26 mmol) to afford (4S)-2-ethoxy-4-(3-fluoro-2-methylphenyl)-4,5-dihydro-1,3-oxazole (20) (0.055 g, 95%): $^1$HNMR ($CDCl_3$) δ: 7.20-7.16 (m, 2H), 6.98-6.93 (m, 1H), 5.35 (dd, 1H), 4.80 (dd, 1H), 4.45-4.37 (m, 2H), 4.04 (t, 1H), 2.19 (s, 3H), 1.43 (t, 3H) ppm; MS: (m/e): 224 (M+1).

Example 5

Synthesis of Amino-Oxazoline

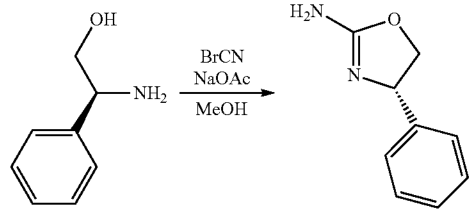

9 21

General procedure for the synthesis of amino-oxazoline: (4S)-4-phenyl-4,5-dihydro-1,3-oxazol-2-amine (21). To (2S)-2-amino-2-phenylethan-1-ol hydrochloride (9) (1.00 g, 7.3 mmol, 1 equiv) in MeOH (36 mL) was added NaOAc (1.80 g, 22 mmol, 3 equiv). The mixture was cooled to 0° C. before cynogen bromide (0.847 g, 8.0 mmol, 1.1 equiv) in MeOH (36 mL) was added dropwise. The mixture was allowed to warm to rt and stirred for 18 h. The mixture was concentrated in vacuo, and resultant residue was covered with EtOAc (50 mL) and stirred for 30 min. The mixture was filtered; the filtrate was concentrated in vacuo; and resultant residue was purified by column chromatography (21) (24 g ISCO MeOH/DCM 0 to 10%) to afford (4S)-4-phenyl-4,5-dihydro-1,3-oxazol-2-amine (0.947 g, 80%): $^1$HNMR ($CDCl_3$) δ: 7.36-7.26 (m, 5H), 5.27 (broad s, 2H), 5.12 (dd, 1H), 4.67 (t, 1H), 4.10 (dd, 1H) ppm; MS: (m/e): 163 (M+1).

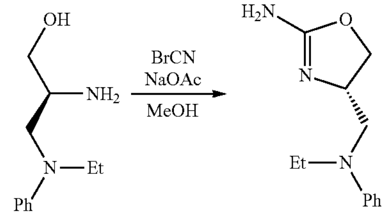

13 22

(4S)-4-{[ethyl(phenyl)amino]methyl}-4,5-dihydro-1,3-oxazol-2-amine (22)

The general procedure for amino-oxazoline synthesis was used starting with (2S)-2-amino-3-[ethyl(phenyl)amino]propan-1-ol (13) (0.620 g, 3.20 mmol) (prepared as described in WO2008/098857) to afford (4S)-4-{[ethyl(phenyl)amino]methyl}-4,5-dihydro-1,3-oxazol-2-amine (22) (0.540 g, 77%): $^1$HNMR ($CDCl_3$) δ: 7.22 (dd, 2H), 6.74 (d, 2H), 6.69 (t, 1H), 4.35-4.29 (m, 2H), 4.12-4.06 (m, 1H), 3.53-3.35 (m, 3H), 3.23 (dd, 1H), 1.13 (t, 3H) ppm; MS: (m/e): 220 (M+1).

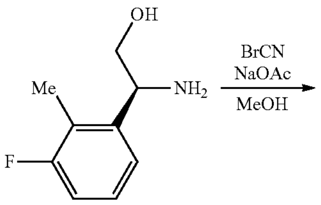

15

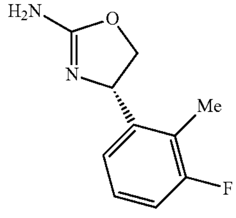

23

(4S)-4-(3-fluoro-2-methylphenyl)-4,5-dihydro-1,3-oxazol-2-amine (23)

The general procedure for amino-oxazoline synthesis was used starting with (2S)-2-amino-2-(3-fluoro-2-methylphenyl)ethan-1-ol hydrochloride (15) (0.300 g, 1.46 mmol) to afford (4S)-4-(3-fluoro-2-methylphenyl)-4,5-dihydro-1,3-oxazol-2-amine (23) (0.196 g, 69%): $^1$HNMR ($CDCl_3$) δ: 7.23-7.14 (m, 2H), 6.97-6.91 (m, 1H), 5.30 (dd, 1H), 4.85 (broad s, 2H), 4.70 (dd, 1H), 3.95 (dd, 1H), 2.19 (s, 3H), ppm; MS: (m/e): 195 (M+1).

Example 6

Synthesis of Bis-Oxazoline Pseudodimer

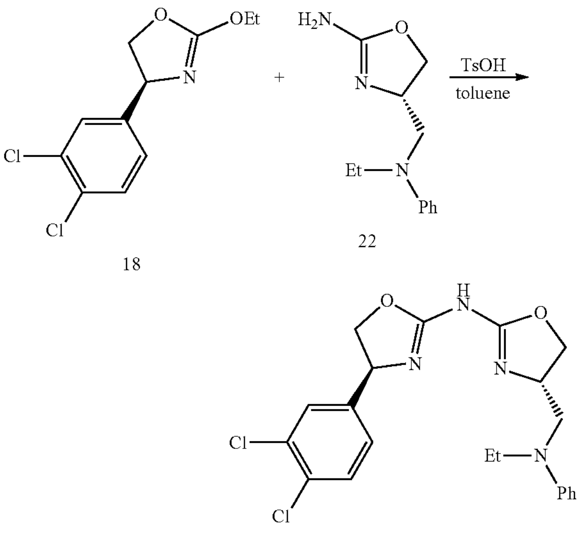

18 22 24

General procedure for the synthesis of bis-oxazoline pseudodimers: (4S)-4-(3,4-dichlorophenyl)-N-[(4S)-4-{[ethyl(phenyl)amino]methyl}-4,5-dihydro-1,3-oxazol-2-yl]-4,5-dihydro-1,3-oxazol-2-amine (24). To ether 18 (0.025 g, 0.096 mmol, 1 equiv) and amine 22 (0.030 g, 0.106 mmol, 1.1 equiv) in toluene (1.00 mL) was added TsOH—$H_2O$ (0.0006 g, 0.003 mmol, 0.03 equiv). The mixture was heated to 50° C. for 18 h. After cooling to rt, it was concentrated and purified by prep TLC to afford (4S)-4-(3,4-dichlorophenyl)-N-[(4S)-4-{[ethyl(phenyl)amino]methyl}-4,5-dihydro-1,3-oxazol-2-yl]-4,5-dihydro-1,3-oxazol-2-amine (24) (0.0031 g, 7.5%): $^1$HNMR ($CDCl_3$) δ: 7.36 (s, 1H), 7.31-7.21 (m, 2H), 7.14 (d, 1H), 7.07-7.05 (m, 1H), 6.83-6.79 (m, 1H), 6.69 (t, 1H), 6.42 (d, 1H), 4.97 (dd, 1H), 4.73 (t, 1H), 4.42-4.39 (m, 1H), 4.23 (t, 1H), 3.97 (t, 1H), 3.85-3.80 (m, 1H) 3.15-3.04 (m, 2H), 2.61 (dd, 1H), 2.34 (dd, 1H), 0.96 (t, 3H) ppm; MS: (m/e): 433, 435 (M+1).

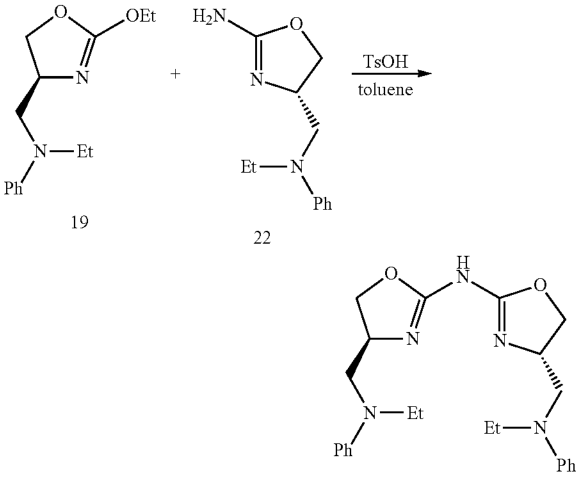

19 22 25

(4S)-4-{[ethyl(phenyl)amino]methyl}-N-[(4S)-4-{[ethyl(phenyl)amino]methyl}-4,5-dihydro-1,3-oxazol-2-yl]-4,5-dihydro-1,3-oxazol-2-amine (25). The general procedure for bis-oxazoline synthesis was used with ether 19 (0.022 g, 0.10 mmol) and amine 22 (0.031 g, 0.11 mmol) to afford (4S)-4-{[ethyl(phenyl)amino]methyl}-N-[(4S)-4-{[ethyl(phenyl)amino]methyl}-4,5-dihydro-1,3-oxazol-2-yl]-4,5-dihydro-1,3-oxazol-2-amine (25) (0.0022 g, 4.7%): $^1$HNMR ($CDCl_3$) δ: 7.25 (t, 4H), 6.76 (t, 2H), 6.63 (d, 4H), 4.33 (t, 2H), 4.17-4.13 (m, 2H), 4.05 (t, 2H), 3.43-3.37 (m, 4H), 3.25-3.18 (m, 2H), 2.91 (dd, 2H), 0.96 (t, 6H) ppm; MS: (m/e): 422 (M+1).

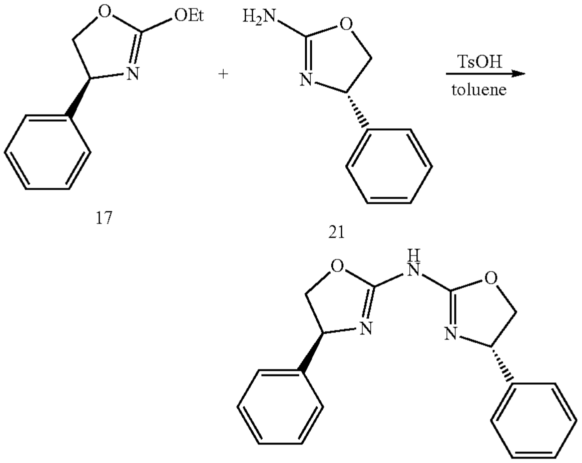

17 21 26

(4S)-4-phenyl-N-[(4S)-4-phenyl-4,5-dihydro-1,3-oxazol-2-yl]-4,5-dihydro-1,3-oxazol-2-amine (26)

The general procedure for bis-oxazoline synthesis was used with ether 17 (0.0162 g, 0.10 mmol) and amine 21 (0.021 g, 0.11 mmol) to afford (4S)-4-phenyl-N-[(4S)-4-phenyl-4,5-dihydro-1,3-oxazol-2-yl]-4,5-dihydro-1,3-oxazol-2-amine (26) (0.0097 g, 32%): $^1$HNMR ($CDCl_3$) δ: 7.35-7.24 (m, 6H), 6.89-6.85 (m, 4H), 4.66 (t, 2H), 4.47 (t, 2H), 3.95 (t, 2H) ppm; MS: (m/e): 308 (M+1).

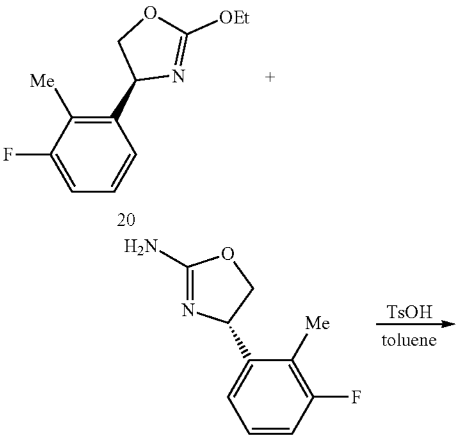

20 23

-continued

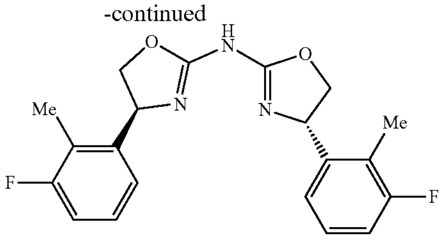

27

(4S)-4-(3-fluoro-2-methylphenyl)-N-[(4S)-4-(3-fluoro-2-methylphenyl)-4,5-dihydro-1,3-oxazol-2-yl]-4,5-dihydro-1,3-oxazol-2-amine (27). The general procedure for bis-oxazoline synthesis was used with ether 20 (0.0304 g, 0.14 mmol) and amine 23 (0.042 g, 0.15 mmol) to afford (4S)-4-(3-fluoro-2-methylphenyl)-N-[(4S)-4-(3-fluoro-2-methylphenyl)-4,5-dihydro-1,3-oxazol-2-yl]-4,5-dihydro-1,3-oxazol-2-amine (27) (0.0233 g, 45%): $^1$HNMR ($CDCl_3$) δ: 6.96 (q, 2H), 6.90 (t, 2H), 6.71 (d, 2H), 4.95 (t, 2H), 4.45 (t, 2H), 3.90 (t, 2H), 2.12 (s, 6H) ppm; MS: (m/e): 372 (M+1).

Example 7

TAAR1 Biodata $EC_{50}$ (the effective concentration of an agonist that produces half of the maximal effect) and $E_{max}$ (the maximal cAMP level generated by the biding of a ligand) can be used as a measure of potency. In some embodiments, the TAAR1 agonists or partial agonists of the present disclosure have $EC_{50} \leq 10$ μm, or $EC_{50} \leq 1$ μm. An in vitro cAMP assay (agonist activity assay) is described below.

cAMP Hunter cell lines were expanded from freezer stocks according to standard procedures. Cells were seeded in a total volume of 20 μL into white walled, 384-well microplates and incubated at 37° C. overnight prior to testing. cAMP modulation was determined using the HitHunter™ cAMP XS+ assay (DiscoverX, Fremont, Calif.).

On the day of test, media was aspirated from cells and replaced with 15 μL HBSS/10 mM HEPES. A plate centrifuge was used for the media exchange, and the plate centrifuge was immediately stopped once its speed hit 270 RPM.

5 μL of 4× compound (prepared in HBSS/10 mM HEPES/4% DMSO) was added to cells and incubated at 37° C. for 30 minutes. Final assay vehicle concentration was 1%.

5 μL of cAMP XS+ Antibody reagent was then added, followed by 20 μL of ED/CL lysis mix. The mixture was incubated at room temperature for 60 minutes. 20 μL of EA reagent was added, and the mixture was incubated at room temperature for 120 minutes.

Microplates were read following signal generation with a PerkinElmer Envision™ instrument (Waltham, Mass.) for chemiluminescent signal detection. Compound activity was analyzed using CBIS Data Analysis Suite (ChemInnovation, CA).

Five compounds were tested in the assay, and their $EC_{50}$ and $E_{max}$ values are reported in the table below.

| Compounds | hTAAR1 $EC_{50}$ (mean ± SEM(n)) | hTAAR1 $E_{max}$ (mean ± SEM(n)) |
|---|---|---|
| Compound (8) | >10 μM(3) | 16.7 ± 7.2% (3) |
| Compound (24) | >10 μM(3) | 34.3 ± 8.7% (3) |
| Compound (25) | 4070.230 ± 1065.450 nM(3) | 60.7 ± 9.4% (3) |

-continued

| Compounds | hTAAR1 $EC_{50}$ (mean ± SEM(n)) | hTAAR1 $E_{max}$ (mean ± SEM(n)) |
|---|---|---|
| Compound (26) | >10 μM(3) | 3.6 ± 0.9% (3) |
| Compound (27) | 398.150 ± 65.550 nM(3) | 67.5 ± 3.4% (3) |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The present application claims benefit to U.S. Provisional Application No. 62/331,710, filed May 4, 2016, which is incorporated herein by reference in its entirety.

All patents, patent applications, and other publications cited herein are fully incorporated by reference herein in their entirety.

What is claimed is:

1. A compound of Formula (I)

I

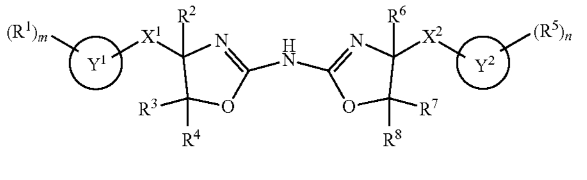

or a pharmaceutically acceptable salt or solvate thereof, wherein each $R^1$ and each $R^5$ are independently:

deuterium, tritium, lower alkyl, lower alkoxy, lower alkyl substituted by one or more same or different halogens, lower alkoxy substituted by one or more same or different halogens, halogen, phenyl unsubstituted or substituted by one or more same or different halogens, phenyloxy, benzyl, benzyloxy, —COO-lower alkyl, —O—$(CH_2)_o$—O-lower alkyl, —NH-cycloalkyl, cycloalkyl, piperidin-1-yl, or tetrahydropyran-4-yloxy;

$X^1$ and $X^2$ are each independently a bond, —$CH(R^{20})$—, —$CH(R^{20})CH(R^{21})$—, —$OCH(R^{20})$—, —$N(R^{20})CH(R^{21})$—, —$CH_2OCH(R^{20})$—, —$CH_2CH_2CH_2$—, —$SCH(R^{20})$—, —$S(O)_2CH(R^{20})$—, —$CH_2SCH_2$—, —$CH_2N(R^{20})CH_2$—, -cycloalkyl-$CH_2$— or —$Si(R^{20})(R^{21})CH_2$—, wherein $R^{20}$ and $R^{21}$ are each independently hydrogen, lower alkyl, lower alkyl substituted by one or more same or different halogens, or benzyl unsubstituted or substituted by one or more same or different substituents selected from the group consisting of alkoxy and halogen;

$R^2$ and $R^6$ are each independently hydrogen, phenyl, or lower alkyl;

$R^3$, $R^4$, $R^7$, and $R^8$ are each independently hydrogen, lower alkyl, lower alkoxy, lower alkyl substituted by one or more same or different halogens, or lower alkoxy substituted by one or more same or different halogens;

$Y^1$ and $Y^2$ are each independently phenyl, naphthyl, thiophenyl, pyridinyl, cycloalkyl, 1,2,3,4-tetrahydro-naphthalen-2-yl, 2,3-dihydrobenzo[1,4]dioxin-6-yl, benzo[1,3]dioxol-5-yl, pyrimidyl, indanyl, 2,3-dihydroindol-1-yl, or 3,4-dihydro-quinolin-1-yl;

m and n are each independently 0, 1, 2 or 3; and o is 1, 2, or 3, and wherein the compound of Formula (I) is not

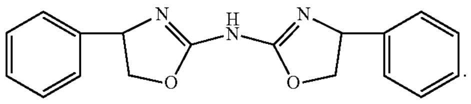 [SMILES: c1ccc(C2COC(NC3=NC(c4ccccc4)CO3)=N2)cc1]

2. The compound according to claim 1, wherein the two oxazoline moieties in Formula (I)

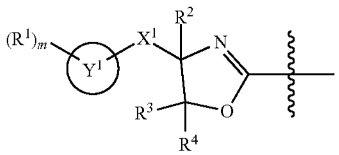

and

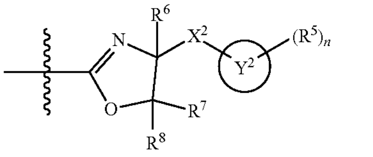

are the same.

3. The compound according to claim 1, wherein the two oxazoline moieties in Formula (I)

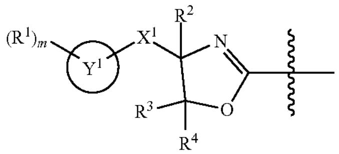

and

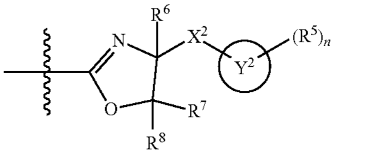

are different.

4. The compound according to claim 1, wherein $X^1$ and $X^2$ are each independently a bond, —$CH(R^{20})$, —$CH(R^{20})CH(R^{21})$—, $OCH_2$—, —$CH_2OCH(R^{20})$—, or —$N(R^{20})CH(R^{21})$—, wherein $R^{20}$ and $R^{21}$ are each independently hydrogen, lower alkyl, or lower alkyl substituted by one or more same or different halogens, or a pharmaceutically acceptable salt thereof.

5. The compound according to claim 1, wherein $Y^1$ and $Y^2$ are, each independently, phenyl, naphthyl, thiophenyl, pyridinyl, cycloalkyl, 1,2,3,4-tetrahydro-naphthalen-2-yl, 2,3-dihydrobenzo[1,4]dioxin-6-yl, or benzo[1,3]dioxol-5-yl, or a pharmaceutically acceptable salt thereof.

6. The compound according to claim 1, wherein each $R^1$ and each $R^5$ are independently:

lower alkyl, lower alkoxy, lower alkyl substituted by one or more same or different halogens, lower alkoxy substituted by one or more same or different halogens, or halogen;

$R^2$ and $R^6$ are hydrogen;

$R^3$ and $R^7$ are each independently hydrogen, lower alkyl, or lower alkyl substituted by one or more same or different halogens; and $R^4$ and $R^8$ are each independently hydrogen, lower alkyl, or lower alkyl substituted by one or more same or different halogens;

or a pharmaceutically acceptable salt thereof.

7. The compound according to claim 1, having Formula (I-A):

I-A

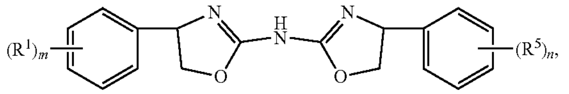

or a pharmaceutically acceptable salt thereof.

8. The compound according to claim 7, having Formula (I-Aa):

I-Aa

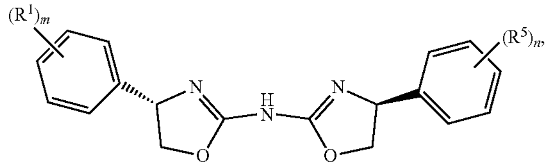

or a pharmaceutically acceptable salt thereof.

9. The compound according to claim 1, having the structure of:

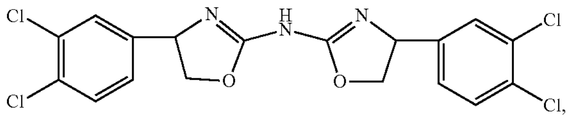

or

-continued

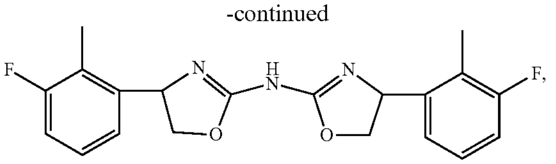

or a pharmaceutically acceptable salt thereof.

10. The compound according to claim 8, having the structure of:

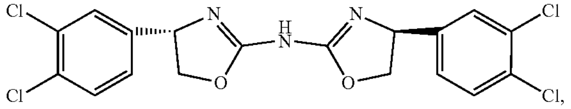

or

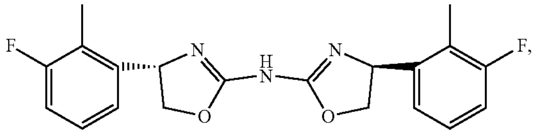

or a pharmaceutically acceptable salt thereof.

11. The compound according to claim 1, having Formula (I-C):

I-C

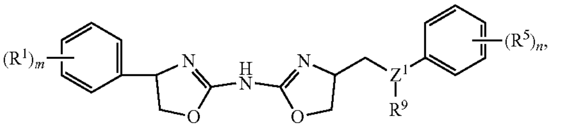

or a pharmaceutically acceptable salt thereof, wherein $Z^1$ is N or CH;

each $R^1$ and each $R^5$ are independently:

lower alkyl, lower alkoxy, lower alkyl substituted by one or more same or different halogens, lower alkoxy substituted by one or more same or different halogens, halogen, or cycloalkyl;

$R^9$ is hydrogen, lower alkyl, or benzyl unsubstituted or substituted by one or more same or different substituents selected from the group consisting of alkoxy or halogen; and m and n are each independently 0, 1, 2, or 3.

12. The compound according to claim 11, having the structure:

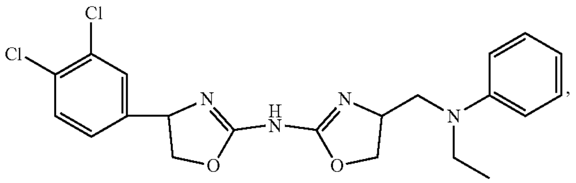 [SMILES: CCN(CC1COC(NC2=NC(c3ccc(Cl)c(Cl)c3)CO2)=N1)c1ccccc1]

or a pharmaceutically acceptable salt thereof.

13. The compound according to claim 12, having the structure:

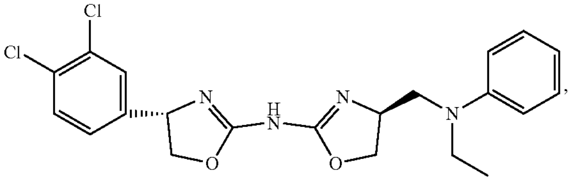 [SMILES: CCN(C[C@H]1COC(NC2=N[C@@H](c3ccc(Cl)c(Cl)c3)CO2)=N1)c1ccccc1]

or a pharmaceutically acceptable salt thereof.

14. A pharmaceutical composition comprising a compound according to claim 1, or a pharmaceutically acceptable salt thereof, and a pharmaceutically acceptable excipient.

15. A method of treating pain comprising administering to a subject in need thereof a therapeutically effective amount of a compound of Formula (I)

I

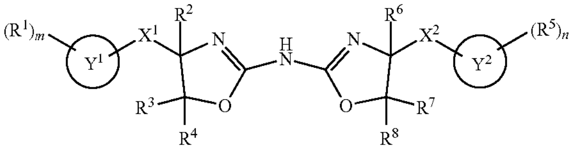

or a pharmaceutically acceptable salt thereof, wherein each $R^1$ and each $R^5$ are independently:

deuterium, tritium, lower alkyl, lower alkoxy, lower alkyl substituted by one or more same or different halogens, lower alkoxy substituted by one or more same or different halogens, halogen, phenyl unsubstituted or substituted by one or more same or different halogens, phenyloxy, benzyl, benzyloxy, —COO-lower alkyl, —O—$(CH_2)_o$—O-lower alkyl, —NH-cycloalkyl, cycloalkyl, piperidin-1-yl, or tetrahydropyran-4-yloxy;

$X^1$ and $X^2$ are each independently a bond, —$CH(R^{20})$—, —$CH(R^{20})CH(R^{21})$—, —$OCH(R^{20})$—, —$N(R^{20})CH(R^{21})$—, —$CH_2OCH(R^{20})$—, —$CH_2CH_2CH_2$—, —$SCH(R^{20})$—, —$S(O)_2CH(R^{20})$—, —$CH_2SCH_2$—, —$CH_2N(R^{20})CH_2$—, -cycloalkyl-$CH_2$— or —$Si(R^{20})(R^{21})CH_2$—, wherein $R^{20}$ and $R^{21}$ are each independently hydrogen, lower alkyl, lower alkyl substituted by one or more same or different halogens, or benzyl unsubstituted or substituted by one or more same or different substituents selected from the group consisting of alkoxy and halogen;

$R^2$ and $R^6$ are each independently hydrogen, phenyl, or lower alkyl;

$R^3$, $R^4$, $R^7$, and $R^8$ are each independently hydrogen, lower alkyl, lower alkoxy, lower alkyl substituted by one or more same or different halogens, or lower alkoxy substituted by one or more same or different halogens;

$Y^1$ and $Y^2$ are each independently phenyl, naphthyl, thiophenyl, pyridinyl, cycloalkyl, 1,2,3,4-tetrahydro-naphthalen-2-yl, 2,3-dihydrobenzo[1,4]dioxin-6-yl, benzo[1,3]dioxol-5-yl, pyrimidyl, indanyl, 2,3-dihydroindol-1-yl, or 3,4-dihydro-quinolin-1-yl;

m and n are each independently 0, 1, 2 or 3; and o is 1, 2, or 3.

16. A method of activating TAAR1 comprising administering to a subject in need thereof an effective amount of a compound of Formula (I)

I

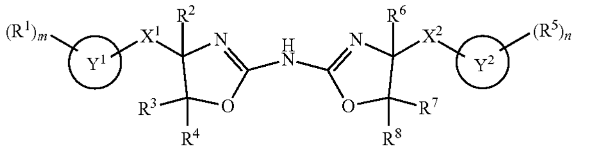

or a pharmaceutically acceptable salt thereof, wherein each $R^1$ and each $R^5$ are independently:

deuterium, tritium, lower alkyl, lower alkoxy, lower alkyl substituted by one or more same or different halogens, lower alkoxy substituted by one or more same or different halogens, halogen, phenyl unsubstituted or substituted by one or more same or different halogens, phenyloxy, benzyl, benzyloxy, —COO-lower alkyl, —O—$(CH_2)_o$—O-lower alkyl, —NH-cycloalkyl, cycloalkyl, piperidin-1-yl, or tetrahydropyran-4-yloxy;

$X^1$ and $X^2$ are each independently a bond, —$CH(R^{20})$—, —$CH(R^{20})CH(R^{21})$—, —$OCH(R^{20})$—, —$N(R^{20})CH(R^{21})$ $CH_2OCH(R^{20})$—, —$CH_2CH_2CH_2$—, —$SCH(R^{20})$—, —$S(O)_2CH(R^{20})$—, —$CH_2SCH_2$—, —$CH_2N(R^{20})CH_2$—, -cycloalkyl-$CH_2$— or —$Si(R^{20})(R^{21})CH_2$—, wherein $R^{20}$ and $R^{21}$ are each independently hydrogen, lower alkyl, lower alkyl substituted by one or more same or different halogens, or benzyl unsubstituted or substituted by one or more same or different substituents selected from the group consisting of alkoxy and halogen;

$R^2$ and $R^6$ are each independently hydrogen, phenyl, or lower alkyl;

$R^3$, $R^4$, $R^7$, and $R^8$ are each independently hydrogen, lower alkyl, lower alkoxy, lower alkyl substituted by one or more same or different halogens, or lower alkoxy substituted by one or more same or different halogens;

$Y^1$ and $Y^2$ are each independently phenyl, naphthyl, thiophenyl, pyridinyl, cycloalkyl, 1,2,3,4-tetrahydro-naphthalen-2-yl, 2,3-dihydrobenzo[1,4]dioxin-6-yl, benzo[1,3]dioxol-5-yl, pyrimidyl, indanyl, 2,3-dihydroindol-1-yl, or 3,4-dihydro-quinolin-1-yl;

m and n are each independently 0, 1, 2 or 3; and o is 1, 2, or 3.

17. The compound according to claim 11, having Formula (I-Ca):

I-Ca

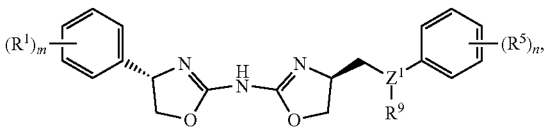

or a pharmaceutically acceptable salt thereof.

18. The compound according to claim 11, wherein $R^9$ is hydrogen or lower alkyl, or a pharmaceutically acceptable salt thereof.

19. The compound according to claim 11, wherein $Z^1$ is CH, or a pharmaceutically acceptable salt thereof.

* * * * *